United States Patent [19]
Falkner et al.

[11] Patent Number: 5,766,882
[45] Date of Patent: Jun. 16, 1998

[54] RECOMBINANT POXVIRUSES WITH FOREIGN DNA IN ESSENTIAL REGIONS

[75] Inventors: Falko-Günter Falkner; Georg Holzer; Friedrich Dorner, all of Vienna, Austria

[73] Assignee: Immuno Aktiengesellschaft, Vienna, Austria

[21] Appl. No.: 616,133

[22] Filed: Mar. 14, 1996

Related U.S. Application Data

[63] Continuation-in-part of Ser. No. 235,392, Apr. 29, 1994, abandoned.
[51] Int. Cl.$^6$ .............................. C12N 5/00; C12N 15/00; C12P 21/06
[52] U.S. Cl. ................. 435/69.1; 435/172.3; 435/320.1; 435/325; 935/32; 935/60; 935/66; 935/57
[58] Field of Search ............................. 435/320.1, 69.1, 435/70.3, 91.1, 91.42, 172.1, 172.3, 325, 349, 363, 366, 375; 514/44; 424/199.1, 232.1, 93.2; 536/24.1

[56] References Cited

U.S. PATENT DOCUMENTS

| | | | |
|---|---|---|---|
| 4,722,848 | 2/1988 | Paoletti et al. | 424/89 |
| 5,110,587 | 5/1992 | Paoletti et al. | 424/89 |
| 5,155,020 | 10/1992 | Paoletti | 435/69.1 |
| 5,174,993 | 12/1992 | Paoletti | 424/89 |
| 5,204,243 | 4/1993 | Paoletti | 435/69.1 |
| 5,225,336 | 7/1993 | Paoletti | 435/320.1 |
| 5,338,683 | 8/1994 | Paoletti | 435/320.1 |
| 5,364,773 | 11/1994 | Paoletti et al. | 435/69.1 |
| 5,453,364 | 9/1995 | Paoletti | 435/69.3 |
| 5,494,807 | 2/1996 | Paoletti et al. | 435/69.3 |
| 5,505,941 | 4/1996 | Paoletti | 424/93.2 |
| 5,583,028 | 12/1996 | Paoletti et al. | 435/235.1 |

FOREIGN PATENT DOCUMENTS

| | | | |
|---|---|---|---|
| WO 92/05263 | 4/1992 | WIPO | C12H 15/86 |
| 94/03595 | 2/1994 | WIPO | |
| 95/27507 | 10/1995 | WIPO | |
| 96/21727 | 7/1996 | WIPO | |
| WO 96/39177 | 12/1996 | WIPO | A61K 39/12 |
| WO 96/39491 | 12/1996 | WIPO | C12N 7/01 |
| WO 96/40241 | 12/1996 | WIPO | A61K 39/295 |

OTHER PUBLICATIONS

Falkner et al., "Transient Dominant Selection of Recombinant Vaccinia Viruses", Journal of Virology, (1990), pp. 3108–3111.

Perkus et al., "Cloning and Expression of Foreign Genes in Vaccinia Virus, Using a Host Range Selection System", Journal of Virology, (1989), pp. 3829–3836.

Barrett et al., "Large-Scale Production and Purification of a Vaccinia Recombinant-Derived HIV-1 gp 160 and Analysis of Its Immunogenicity", AIDS Research and Human Retroviruses, vol. 5, No. 2, 1989, pp. 159–171.

Boshart et al., "A Very Strong Enhancer is Located Upstream of an Immediate Early Gene of Human Cytomegalovirus", Cell, vol. 41, Jun. 1985, pp. 521–530.

Broyles et al., "DNA–dependent ATPase Activity Associated with Vaccinia Virus Early Transcription Factor", The Journal of Biological Chemistry, vol. 263, No. 22, Aug. 1988, pp. 10761–10765.

Broyles et al., "Purification of a Factor Required for Transcription of Vaccinia Virus", The Journal of Biological Chemistry, vol. 263, No. 22, Aug. 1988, pp. 10754–10760.

Broyles et al., "The Small Subunit of the Vaccinia Virus Early Transcription Factor Contacts the Transcription Promoter DNA", Journal of Virology, vol. 67, No. 9, Sep. 1993, pp. 5677–5680.

Chakrabarti et al., "Vaccinia Virus Expression Vector: Coexpression of β–Galactosidase Provides Visual Screening of Recombinant Virus Plaques", Mol. Cell. Biol., vol. 5, No. 12, Dec. 1985, pp. 3403–3409.

Condit et al., "Isolation, Characterization, and Physical Mapping of Temperature–Sensitive Mutants of Vaccinia Virus", Virology, vol. 128, 1983, pp. 429–443.

Gunning et al., "A Human β–actin Expression Vector System Directs High–level Accumulation of Antisense Transcripts", Proc. Natl. Acad. Sci. USA, vol. 84, Jul. 1987, pp. 4831–4835.

Hunt et al., "Conserved Features of Eukaryotic hsp70 Genes Revealed by Comparison with the Nucleotide Sequence of Human hsp70", Proc. Natl. Acad. Sci. USA, vol. 82, Oct. 1985, pp. 6455–6459.

Isaacs et al., "Reverse Guanine Phosphoribosyltransferase Selection of Recombinant Vaccinia Viruses", Virology, vol. 178, 1990, pp. 626–630.

Kane et al., "Vaccinia Virus Morphogenesis is Blocked by a Temperature–Sensitive Mutation in the 17 Gene that Encodes a Virion Component", J. of Virology, vol. 67, No. 5, May 1993, pp. 2689–2698.

M. Kriegler, "Gene Transfer and Expression, A Laboratory Manual", pp. 47–56.

Mackett et al., "Vaccinia Virus: A Selectable Eukaryotic Cloning and Expression Vector", Proc. Natl. Acad. Sci. USA, vol. 79, Dec. 1982, pp. 7415–7419.

Mann et al., "Construction of a Retrovirus Packaging Mutant and Its Use to Produce Helper–Free Defective Retrovirus", Cell, vol. 33, May 1983, pp. 153–159.

Merchlinsky et al., "Introduction of Foreign DNA into the Vaccinia Virus Genome by in Vitro Ligation: Recombination–Independent Selectable Cloning Vectors", Virology, vol. 190, 1992, pp. 522–526.

(List continued on next page.)

*Primary Examiner*—Bruce R. Campell
*Attorney, Agent, or Firm*—Foley & Lardner

[57] ABSTRACT

Defective poxviruses that lack a function imparted by an essential region of its parental poxvirus are provided for protein production and vaccination. A DNA polynucleotide encoding a protein is inserted into the defective poxvirus and placed under transcriptional control of a promoter. The defective poxvirus is viable when the lost function of the essential region is complemented by a host cell, transgenic animal or helper virus.

44 Claims, 8 Drawing Sheets

OTHER PUBLICATIONS

Miner et al., "Vaccinia Virus: A versatile tool for molecular biologists", TIBTECH, vol. 8, Jan. 1990, pp. 20–25.

Panicali et al., "Construction of Poxviruses as Cloning Vectors: Insertion of the Thymidine Kinase Gene from Herpes Simplex Virus into the DNA of Infectious Vaccinia Virus", Proc. Natl. Acad. Sci. USA, vol. 79, Aug. 1992, pp. 4927–4931.

Scheiflinger et al., "Construction of Chimeric Vaccinia Viruses by Molecular Cloning and Packaging", Proc. Natl. Acad. Sci. USA, vol. 89, Nov. 1992, pp. 9977–9981.

Taylor et al., "Fowlpox Virus as a Vector in Non-avian Species", Vaccine, vol. 6, Dec. 1988, pp. 466–468.

Wigler et al., "Transfer of Purified Herpes Virus Thymidine Kinase Gene to Cultured Mouse Cells", Cell, vol. 11, May 1977, pp. 223–232.

Jindal et al., "Vaccinia Virus Infection Induces a Stress Response that Leads to Association of Hsp70 with Viral Proteins", J. of Virology, vol. 66, No. 9, Sep. 1992, pp. 5357–5362.

Fenner et al., "Vaccinia Virus as a Vector for Vaccine Antigens" The Orthopoxvirus, Chapter 12, 1988, pp. 353–377.

Falkner et al., "Transient Dominant Selection of Recombinant Vaccinia Viruses", J. of Virology, vol. 64, No. 6, Jun. 1990, pp. 3108–3111.

Falkner et al., "*Escherichia coli gpt* Gene Provides Dominant Selection for Vaccinia Virus Open Reading Frame Expression Vectors", J. of Virology, vol. 62, No., 6, Jun. 1988, pp. 1849–1854.

Gershon et al., "Early Transcription Factor Subunits are Encoded by Vaccinia Virus Late Genes", Proc. Natl. Acad. Sci. USA, vol. 87, Jun. 1990, pp. 4401–4405.

Goebel et al., "The Complete DNA Sequence of Vaccinia Virus", Virology, vol. 179, 1990, pp. 247–266.

Graham et al., "Transformation of Rat Cells by DNA of Human Adenovirus 5", Virology, vol. 54, 1973, pp. 536–539.

Wittek et al., "Mapping of a Gene Coding for a Major Late Structural Polypeptide on the Vaccinia Virus Genome", J. of Virology, vol. 49, No. 2, Feb. 1984, pp. 371–378.

Weir et al., "Use of a Bacterial Expression Vector to Identify the Gene Encoding a Major Core Protein of Vaccinia Virus", J. of Virology, vol. 56, No. 2, Nov. 1985, pp. 534–540.

Lai et al., "Structural and Functional Properties of the 14–kDa Envelope Protein of Vaccinia Virus Synthesized in *Escherichia coli*", The J. of Biol. Chem., vol. 265, No. 36, Dec. 1990, pp. 22174–22180.

Zhang et al., "Immature Viral Envelope Formation is Interrupted at the Same State by Iac Operator–Mediated Repression of the Vaccinia Virus D13L Gene and by the Drug Rifampicin", Virology, vol. 187, 1992, pp. 643–653.

Zhang et al., "Vaccinia virus Morphogenesis is Interrupted when Expression of the Gene Encoding and 11–Kilodalton Phosphorylated Protein is Prevented by the *Escherichia coli* lac Repressor", J. of Virology, vol. 65, No. 11, Nov. 1991, pp. 6101–6110.

Yanisch–Perron et al., "Improved M13 Phage Cloning Vectors and Host Strains: Nucleotide Sequences of the M13mph 18 and pUC19 Vectors", Gene, vol. 33, 1985, pp. 103–119.

Towbin et al., "Electrophoretic Transfer of Proteins from Polyacrylamide Gels to Nitrocellulose Sheets: Procedure and some applications", Proc. Natl. Acad. Sci. USA, vol. 76, No. 9, Sep. 1979, pp. 4350–5354.

Sutter et al. Journal of Virology 68(7): 4109–4116 (Jul. 1994).

Q. Wang et al. Gene Therapy 2 : 775–83 ('95).

V. Krougliak et al. Human Gene Therapy 6:1575–86 ('95).

B. Moss, Ch. 31 in Virology, ed. by B.N. Fields et al., Raven Press, NY '85 pp. 685–703.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGTACTCCAT GGAAAGATAT ACAGATTTAG        30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ATCCCGGGTT TTAGAGACTT TGAAGCTACT        30

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CTCGAGATCT GGCGTTTTC CATAGGCT        28

( 2 ) INFORMATION FOR SEQ ID NO:4:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCAAGCTTGC CCATGGGCAT GCTCTGCAGG TCGACTCTAG AGGATC        46

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGAGATCTCG AGTCCGGACT TAAGAGCGCC CAATACGCAA ACG        43

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CATGCCCATG GTCATGATGT CTTCCTGTGT GAAATTGTTA TC    42

( 2 ) INFORMATION FOR SEQ ID NO:7:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TCGACCATGG ACAAGCTTAT CGATCCCGGG AATTCGGTAC CGTCGACCTG CAGGTGCACG    60

GGCCCAGATC TGACTGACTG A    81

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AGGAGTTAAT GAGGCCAATG GA    22

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GACATAGGTA TAGAATCCGG A    21

( 2 ) INFORMATION FOR SEQ ID NO:10:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AGTTTAAACG GCGCGCCGG GCTCGAGAGG CCTCTGCAGA TGCATCCATG GGGATCCGAA    60

TTC    63

( 2 ) INFORMATION FOR SEQ ID NO:11:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GAATTCGGAT CCCCATGGAT GCATCTGCAG AGGCCTCTCG AGCCCGGGCG CGCCGTTTAA    60

ACT    63

( 2 ) INFORMATION FOR SEQ ID NO:12:

( i ) SEQUENCE CHARACTERISTICS:

( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO:12:

GATCCTACGT ATCTAGAATT AATTAATGGC CAATTTAAAT GCCCGGGA  48

( 2 ) INFORMATION FOR SEQ ID NO:13:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AATTTCCCGG GCATTTAAAT TGGCCATTAA TTAATTCTAG ATACGTAG  48

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CTGCAGATGC GATATATAGT AAGTCCGCA  29

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

ACCCGGGTTT AATTTATTTG TGCTCTTC  28

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TTCAGATAAT GAACTTACCA  20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TTGGAGAACT TGATACGCCG  20

( 2 ) INFORMATION FOR SEQ ID NO:18:

( i ) SEQUENCE CHARACTERISTICS:
        ( A ) LENGTH: 41 base pairs
        ( B ) TYPE: nucleic acid ( C ) STRANDEDNESS: single
( D ) TOPOLOGY: linear ( x i ) SEQUENCE DESCRIPTION: SEQ ID NO:18:

CTAGGCTTTT GCAAAAGCT CCTCGACCAT GGTGTCTTCA A    41

( 2 ) INFORMATION FOR SEQ ID NO:19:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AGCTTTGAAG ACACCATGGT CGAGGAGCTT TTTGCAAAAG C    41

( 2 ) INFORMATION FOR SEQ ID NO:20:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CTCGATAGGG CCCTAGGCCT ACTAGTACTA AGCTTCTGCA GGTCGACTCT AGAGGACCCC    60

GGGGAATTCA ATCGATTCGA G    81

( 2 ) INFORMATION FOR SEQ ID NO:21:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

AGCTTCTCGA GCTGGAGGAG CAGAAGCTGA TCTCCGAGGA GGATCTGCTG AGAAAGAGAT    60

AACCC    65

( 2 ) INFORMATION FOR SEQ ID NO:22:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GGGTTATCTC TTTCTCAGCA GATCCTCCTC GGAGATCAGC TTCTGCTCCT CCAGCTCGAG    60

A    61

( 2 ) INFORMATION FOR SEQ ID NO:23:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

Leu Glu Glu Gln Lys Leu Ile Ser Glu Glu Asp Leu Leu Arg Lys Arg
1               5                   10                  15

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:24:

GACTCCATGG CGGAATTTGA AGATCAACTC    30

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:25:

ATGCCTCGAG TTCAGCATTA CTTGATATAG TA    32

RECOMBINANT POXVIRUSES WITH FOREIGN DNA IN ESSENTIAL REGIONS

This application is a CIP and claims priority under 35 USC §120 to U.S. application Ser. No. 08/235,392, filed Apr. 29, 1994, now abandoned, which is hereby incorporated by reference.

BACKGROUND OF THE INVENTION

Recombinant poxviruses have been used as vectors for expression of foreign genes. Such foreign genes can be from a variety of sources, such as animals, plants, protozoa, fungi, bacteria, and viruses. Additionally, recombinant poxviruses can be used to express chimeric genes and genes of synthetic origins. Typically, chimeric genes and synthetic genes are DNA sequences that are derived from or based on naturally-occurring sequences. For example, cDNA sequences generated from RNA transcripts, including those from retroviruses, can be expressed with recombinant poxvirus vectors.

The poxvirus vectors in present use contain foreign DNA inserted into genomic regions that are not essential to the viability of the virus. These poxviruses expressing foreign genes are usually constructed by insertion of the foreign sequences into genomic regions that are non-essential for growth of the virus in cell culture by homologous recombination (Panicali and Paoletti, *Proc. Nat'l Acad. Sci.* USA 79: 4927–31 (1982); Mackett et al., *Proc. Nat'l Acad. Sci.* USA 79: 7415–19 (1982)) or by direct molecular cloning (U.S. Pat. No. 5,445,953; U.S. application Ser. No. 07/914, 738; Scheiflinger et al., *Proc. Nat'l Acad. Sci.* USA, 89: 9977–81 (1992); Marchlinsky and Moss, *Virol.* 190: 522–26 (1992)). Viruses with foreign DNA inserted into non-essential regions can grow autonomously in their host organism and, thus, remain infectious to their respective hosts.

The loss of the products of these non-essential regions does not unduly impair to viability of the recombinant poxvirus. In the case of vaccinia, often considered the prototypic poxvirus, one of the major non-essential regions for insertion is the thymidine kinase gene. When a foreign gene is inserted into the vaccinia thymidine kinase gene, the product of the gene is lost to the virus. Nonetheless, the recombinant vaccinia is able to maintain viability. Other poxviruses are also amenable to similar manipulations in other non-essential regions. For example, recombinant avipox, such as fowlpox, have been based upon the advances made with the orthopoxviruses.

Recombinant vaccinia can be used as live vaccines, as well as in large-scale expression systems. See Miner & Hruby, *TIBTECH* 8: 20–25 (1990); Brochier et al., *Vaccine* 8: 101–04 (1990). Other poxviruses have been used as well. See van der Leek et al., *Veterin. Rec.* 134: 13–18 (1994) (concerning swinepox virus as a vaccine vector); Baxby et al., *Vaccine* 10: 8–9 (1992) and Taylor et al., *Virol.* 187: 321–28 (1992) (concerning the use of canarypox as a vaccine vector). The use of recombinant viruses for large-scale expression of proteins and as vaccines presents significant risks, however, because the viruses retain an infective capability. Accordingly, costly precautions and cumbersome procedures are required when handling recombinant vaccinia. For example, thermal inactivation of all media, fluids and contaminated lab ware is required, as well as special training for all personnel handling the virus.

Several approaches have been considered for minimizing the need for the elaborate precautions employed presently. For example, highly attenuated vaccinia strains have been developed, such as MVA (for modified vaccinia Ankara. See Sutter et al., *J. Virol.* 68: 4109–116 (1994). These highly attenuated strains have limited infectivities. Accordingly, production of proteins with these highly attenuated viruses was hoped to be possible. Unfortunately, these highly attenuated strains have slow and limited growth, which makes them ill-suited for large-scale protein production.

Other attenuated or range-restricted vaccinia viruses have been constructed for expression of foreign genes. U.S. Pat. No. 5,453,364 discloses host range mutants of vaccinia strain WR, which were constructed by inserting a neomycin resistance gene into host range genes, such as K1L or C7L, which are non-essential because the resultant mutant virus is still viable and infective in certain cell types. See Johnson et al., *Virol.* 196: 381–401 (1993). For example, the mutant viruses can replicate on CEF, BCS-40 and VERO cells, but cannot replicate in MRC-5 cells. The lost host-range function in these mutant viruses is replaced in cis upon recombination with a plasmid containing the foreign gene and the host-range gene.

In addition to the highly attenuated and range-restricted poxviruses, defective strains of other viruses are known. For example, defective retroviruses can be grown in helper cell lines that complement in trans the defect of the virus. See Kriegler, GENE TRANSFER AND EXPRESSION (Stockton Press, 1990) at 33–39; Mann et al., *Cell* 33: 153–59 (1983). Retroviruses are small RNA-containing viruses that multiply by integration into the genome of the host cell, which makes these viruses inappropriate for use as expression vectors or vaccines. The growth of defective herpes virus in helper cells has also been reported. See PCT publication WO 94/03595. Herpes replicates in the nucleus of infected cells, and naked herpes DNA is infectious. Because herpes is a nuclear virus, it has the potential of rescuing its defective gene from the host cell via homologous recombination. Such recombinational events are undesirable and dangerous because the defective herpes virus can potentially return to a wild-type state, which results in increased infectivity and virulence, as well as the loss of the inserted foreign gene.

Because of the need for safer recombinant poxvirus expression systems and vaccines, novel approaches need to be undertaken to engineer fundamentally different recombinant poxviruses. The approach described herein inserts foreign genes into an essential region, such as a gene encoding an essential product, of the poxvirus, which renders the poxvirus non-viable. The loss of the product from the essential region is complemented in trans by the same or similar product from other sources, such as recombinant host cells, helper virus or transgenic animals.

SUMMARY OF THE INVENTION

It thus is an object of the present invention to provide recombinant poxviruses capable of expressing foreign DNA polynucleotides.

It is another object of the present invention to provide recombinant poxviruses that are defective because they lack a function imparted by a essential region, such as an essential gene, of the poxvirus from which the defective poxvirus is based.

It is another object of the present invention to provide defective poxviruses that possess foreign DNA polynucleotides inserted into essential regions of the poxvirus genome.

It is still another object of the present invention to provide defective poxviruses that have all or part of an essential region deleted.

3

It is still another object of the present invention to provide defective poxviruses that can be used as vaccines.

It is yet another object of the present invention to provide host cells, helper virus or transgenic animals that can complement in trans the lost function of a defective poxvirus.

In accomplishing these and other objects, there are provided, in accordance with one aspect of the present invention, defective poxviruses that lack a function imparted by an essential region, such as a gene encoding an essential product, of its parental poxvirus, the defective poxvirus comprising a foreign DNA polynucleotide under transcriptional control of a promoter. The promoter should be operable with the enzymes of defective poxvirus or within infected host, such promoters include poxvirus promoters. The foreign polynucleotide can be inserted into the essential region or replace the essential region. Additionally, a marker can substitute for the essential region. The foreign polynucleotide can be thereafter inserted into the marker or replace the marker. Preferably, the parental poxvirus is an orthopoxvirus. More preferably, the parental poxvirus is vaccinia and the essential region is one of open reading frames I7L, F18R, D13L, D6R, A8L, J1R, E7L, F11L, E4L, I1L, J3R, J4R, H7R, D4R and A6R.

In accordance with another aspect of the present invention, there are provided cell lines, transgenic animals and helper viruses that have the ability to complement in trans a lost essential function of a defective poxvirus. The ability to complement is imparted by the presence of an essential region in the cell lines, transgenic animals and helper viruses of the present invention.

In accordance with still another aspect of the present invention, there is provided a method of producing a protein, comprising the step of providing a defective poxvirus that lacks a function imparted by an essential region of its parental poxvirus, wherein the defective poxvirus comprises a foreign DNA polynucleotide encoding the protein to be produced, and wherein the DNA polynucleotide is under transcriptional control of a promoter. Complementing cell lines, or other complementing hosts, can be infected with the defective poxvirus, and then the defective poxvirus progeny can be harvested from the complementing host. Additionally, a complementing source, such as a helper virus, can be co-infected along with the defective poxvirus in order to provide complementation.

The promoter should be operable with the defective poxvirus or infected host, such promoters include poxvirus promoters. The DNA polynucleotide can be inserted into the essential region of the parental poxvirus. In another embodiment, a marker, such as the gpt gene, can replace the essential region and, in turn, the DNA polynucleotide can be inserted into the marker or replace the marker. The loss of the marker function indicates that the DNA polynucleotide has been placed within the defective poxvirus.

In accordance with yet another aspect of the present invention, there are provided vaccines comprising defective poxviruses. These defective poxviruses comprise DNA polynucleotides that encode antigens against various pathogens or other entities that may cause disease or other undesirable conditions. The vaccines of the present invention can be constructed in the same or similar manner as the other defective poxviruses of the present invention. Preferably, the vaccine is in a pharmaceutically acceptable carrier.

These and other aspects of the invention disclosed herein will become apparent to the skilled artisan in view of the disclosure contained herein.

DETAILED DESCRIPTION OF THE PREFERRED EMBODIMENTS

Figure 1:
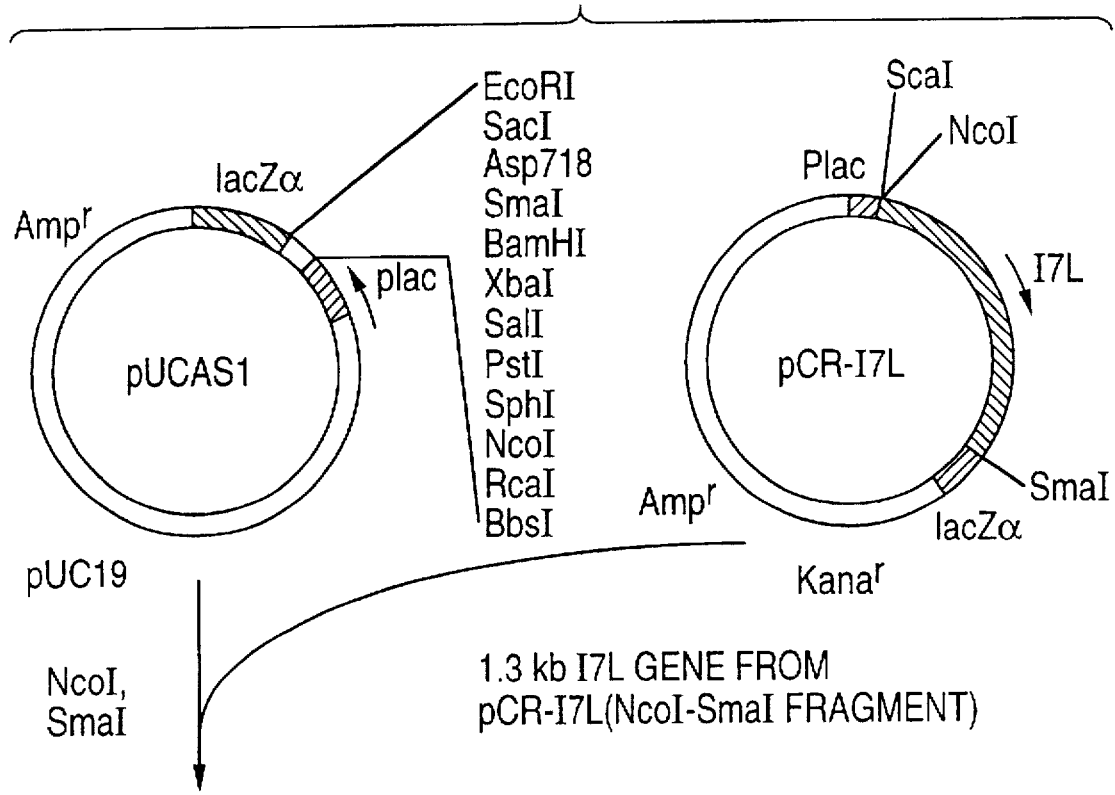
FIG. 1 schematically depicts the construction of plasmid pUCAS-I7L.
Figure 1:
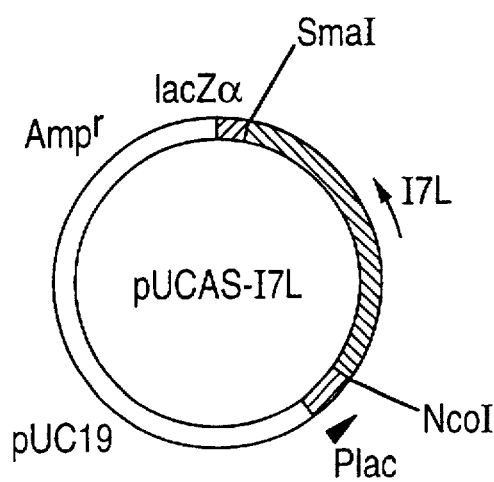

The present invention relates to the use defective poxviruses for the production of proteins. A "defective poxvirus" according to the present invention is a poxvirus that lacks a function imparted by an essential region of a parental poxvirus upon which the defective poxvirus is based and, as a consequence, the defective poxvirus is not viable without complementation of the function by another source. An "essential region" is a region of the poxvirus genome that is needed for viability of the parental poxvirus, and includes open reading frames such as genes. Without a functional "essential region," the mutant poxvirus is no longer viable. In other words, a gene is essential for a virus if its deletion or insertional interruption abolishes growth of the virus in all cell lines known to normally support growth of the virus. Poxviruses suitable for use with the present invention can be any type of poxvirus, including orthopoxviruses and avipoxviruses.

The term "complementation" connotes a restoration of a lost function in trans by another source, such as a host cell, transgenic animal or helper virus. The loss of function is caused by loss by the defective virus of the gene product responsible for the function. Thus, a defective poxvirus is a non-viable form of a parental poxvirus, and is a form that can become viable in the presence of complementation. The host cell, transgenic animal or helper virus contains the sequence encoding the lost gene product (a type of "complementing agent"). The complementing agent should be expressible and stably integrated in the host cell, transgenic animal or helper virus, and preferably would be subject to little or no risk for recombination with the genome of the defective poxvirus.

A parental poxvirus can be a naturally-occurring poxvirus or poxvirus derived therefrom. Preferably, the parental poxvirus is an orthopoxvirus. More preferably, the parental poxvirus in vaccinia, which is considered to be the archetype poxvirus and has been characterized extensively. See Moss, FIELD'S VIROLOGY 2079–2111 (2d ed. 1990); Johnson et al., Virol. 196: 381–401 (1993). Even more preferably, the parental vaccinia is fast growing wild-type virus, such as the Western Reserve ("WR") strain of vaccinia or related strains.

A defective virus is based upon parental poxviruses such as naturally-occurring poxviruses or poxviruses derived from naturally-occurring poxviruses. These derived poxviruses for use as parental poxviruses can be obtained by techniques such as genetic engineering via region-specific and site-specific mutagenesis, in vivo recombination, passaging of virus through host cells in the presence or absence of mutagens, and any combination of the above, as well as other approaches that will become apparent to the person of skill in the art. A defective poxvirus can be based upon any type of poxvirus in which a defect in an essential region can be introduced.

The defective poxvirus can be used as an expression system for proteins. The proteins produced by the defective poxviruses of the present invention are encoded by foreign DNA polynucleotides, such as genes or cDNA versions of RNA transcripts. The term "foreign DNA polynucleotide" refers to a polynucleotide that is not normally present in the parental poxvirus upon which the defective poxvirus is based, or is a polynucleotide that is present in a different location or form than would be found in the parental poxvirus upon which the defective poxvirus is based. The foreign DNA polynucleotides can be from a variety of sources, such as animals, plants, protozoa, fungi, bacteria, and viruses. Due to the large carrying capacity of poxviruses (Taylor and Paoletti, Prog. Vet. Microbiol. Immun. 4: 197–217 (1988)), any DNA polynucleotide that encodes a polypeptide product and is expressible in a eukaryotic environment can be expressed according to the invention.

The defective poxviruses of the present invention can include a promoter that is operable with the defective poxvirus or host infected by the defective poxvirus in order to control the transcription of the foreign DNA polynucleotide within the defective poxvirus. A "promoter" refers to a nucleotide sequence which can initiate and/or direct transcription. Any promoter that is operable with the defective poxvirus or within the infected host can be used in the present invention. "Operability" includes recognizability or readability of the promoter by transcriptional enzymes. Typically, the promoters are poxvirus promoters or synthetic promoters based on promoters of poxvirus origin.

A defective virus can have a foreign DNA polynucleotide inserted into an essential region. A promoter can be linked to the foreign DNA polynucleotide so that it inserted along with the polynucleotide in order for the promoter to have transcription control over the polynucleotide. In the alternative, the promoter for controlling transcription of the foreign DNA polynucleotide can be already present in the defective poxvirus in a location that will allow the promoter to control transcription of the foreign DNA polynucleotide upon its introduction into the virus genome.

The essential region may be fully deleted from the genome of the defective virus so that no homologous recombination is possible between the genome of the complementation source and the defective virus.

A defective virus with such a deletion can only grow in the presence of the complementing source, such as a helper cell line that contains the complementing agent, and thus provides the function of the essential region in trans. Pure stocks of the defective virus can be grown in the helper cell line while growth and multiplication in normal cells and organisms remain impossible. The host range of this type of virus can be restricted to helper cell lines that are specifically engineered to complement in trans the defect of the defective virus.

A marker gene can be used to replace an essential region in the defective poxvirus. The foreign DNA polynucleotide can then be inserted into the marker or replace the marker by homologous recombination. This approach provides a selection system for poxviruses containing inserts of interest. One such marker is the gpt gene, which can be used for reverse gpt-selection in a complementing cell line such as mouse LM(TK$^-$) or STO cells (which are resistent to 6-thioguanine, allowing reverse gpt-selection). This system would result in a fast and efficient way to obtain pure stocks of the desired defective virus. Many rounds of plaque purification may be avoided without active killing of the wild-type virus (that is achieved by negative selection procedures such as reverse gpt-selection or tk-negative selection), which would otherwise be needed to obtain pure stocks.

The present invention is useful for more than large-scale expression of proteins. The defective poxviruses of the present invention can also be used for vaccination purposes. For example, if an appropriate essential gene is inactivated, the defective viruses still retain their ability to penetrate into cells and start an abortive life cycle. Such a gene would be one that is required late in the life cycle and, therefore, the virus still able to replicate its DNA, eventually form immature particles and express its genomic information, which includes the foreign DNA polynucleotide. In this respect, these defective viruses could have an effect similar to the "abortive infection" vaccines mentioned by Taylor and Paoletti, Vaccine 6: 466–68 (1988).

A defective poxvirus that is used as a vaccine would comprise a DNA polynucleotide that encodes an antigen. Antigens are molecules that an organism recognizes as being foreign. These antigens can induce an immunological response from the organism exposed to the antigen. Suitable antigens include proteins of bacterial, viral, fungal and protozoan origin.

The defective poxviruses of the present invention can be grown in host cells that can complement in trans the lost essential function of the defective virus. Typically, these host cells are from cell lines that are specifically engineered to complement the lost function by comprising the gene encoding the product needed for complementation (the complementing agent). Typically, the host cell will have the same or similar poxvirus essential region inserted in the host cell in such a manner that the essential region is expressed by the host cell.

The cell line chosen for complementation and subsequent production of virus and protein should be easy to handle, allow virus plaque formation and be able to carry out all steps required for functionality of the product. Mouse LM(TK$^-$) cells fulfill these requirements and are suitable hosts. The mouse LM(TK$^-$) cell line is also resistent to 6-thioguanine, allowing reverse gpt-selection (Isaacs et al., Virol. 178: 626–30 (1990), a feature that is useful for applying direct selective pressure for the isolation of defective virus. Usually, dominant selection markers like the hygromycin phosphotransferase or the neomycin phosphotransferase genes are used for selection of integration of the complementing gene. The foreign genes may be linked on one plasmid, or, alternatively, co-transformation procedures may be applied (Wigler et al., Cell 11: 223–232 (1977). Other selection markers such the herpes simplex thymidine kinase gene may used with the mouse LM(TK$^-$) cells.

Another cell line that can be used as a complementing cell line for production of proteins is the African Green monkey kidney cell line Vero (ATCC No. CCL 81). This cell line can be grown to high cell densities and has been successfully used for the production of recombinant proteins (Barrett et al., AIDS Res. Hum. Retrovir. 5: 159–71 (1989). Other cell lines that can support all or part of the poxvirus lifecycle can be employed according to the present invention, and preferably are vertebrate cell lines, such as MRC-5 cells, 293 cells, CV-1 cells, BSC-1 cells, or RK 13 cells.

The promoter driving expression of the poxvirus essential region for complementation should be active in the respective cell line. A preferred promoter is the SV40 promoter, which is a strong constitutive promoter that is active in mouse L cells and Vero cells. Other promoters that are usually used for expression in permanent cell lines include the actin promoter, Gunning et al., *Proc. Nat'l Acad. Sci. USA* 84: 4831–35 (1987), and the human cytomegalovirus promoter, Boshardt et al., *Cell* 41: 521–30 (1985), both of which also may be used. A promoter system that may especially be suitable for vaccinia infected cells is the promoter including untranslated upstream regions of the human 70 kD heatshock protein. See Hunt and Morimoto, *Proc. Nat'l Acad. Sci. USA* 82: 6455–59 (1985). Unlike the expression of many other genes, Hsp70 synthesis not deleteriously affected by vaccinia virus host protein shut-off in vaccinia infected cells. See Jindal and Young, *J. Virol.* 66: 5357–62 (1992); Fenner et al., THE ORTHOPOXVIRUSES (Academic Press 1989).

Other hosts that are susceptible to the defective poxviruses include animals transgenic for the vaccinia essential gene (referred to as "complementing transgenic animals"). Such animals provide the complementing function in every somatic cell or in a preferred tissue, which depends on the promoter chosen to express the poxvirus essential gene in the complementing transgenic animal. Such animals, preferably mice, would constitute safe models for poxvirus infection studies and related studies. Selective expression of the transgene in a defined organ may also allow tissue specific gene expression studies and/or studies on the selective function or dysfunction of the respective organ.

Essential gene products that are suited as complementing agents include in general gene products that are required late in the life cycle, such as those involved in morphogenesis or other post-replication events, as well as enzymes and regulatory proteins.

One essential gene product that is a suitable complementing agent is the 47-kDa protein (the "I7-protein") encoded by open reading frame ("orf") I7L, which is believed to be involved in viral genome organization. See Kane and Shuman, *J. Virol.* 67: 2689–98 (1993). The I7-protein is encapsulated with the virus core. A temperature sensitive (ts) mutation (ts16) exists. See Condit et al., *Virol.* 128: 429–43 (1983). The gene therefore fulfills a classical requirement of an essential gene, the existence of a conditional lethal (ts) mutant.

Essential gene products that are suited as complementing agents include also the 11kDa phosphoprotein (Wittek et al., *J. Virol.* 49: 371–78 (1984) encoded by the F18R open reading frame of WR wild-type virus (F17R of vaccinia Copenhagen, Goebel et al., *Virol.* 179: 247–66 (1990)). The 11 kDa phosphoprotein encoded by the F18R open reading frame is an essential gene that is required for correct virion assembly (Zhang and Moss, *Virol.* 65: 6101–10 (1991). Conditional lethal vaccinia mutants in which expression of the 11 kDa protein can be prevented form immature particles with aberrant internal structures. However, F18R is overlaps with the orf A (Goebel et al., loc. cit.) and, therefore, would not be the protein of first choice.

Another essential gene product that is suited as complementing agent is the 65kDa protein encoded by the D13L orf. This protein is expressed late in infection. If expression is prevented, replication is unaffected while viral morphogenesis is blocked at an early stage. See Zhang and Moss, *Virol.* 187: 643–53 (1992).

Enzymes and regulatory proteins are also suitable as complementing agents, especially in view that these proteins need only be present in catalytic amounts, which can be easily provided by the complementing cell line. The subunits of the vaccinia virus early transcription factor ("VETF") are suitable in this respect.

The VETF is essential for the initiation of transcription of "early" vaccinia genes. Vaccinia RNA polymerase lacking VETF is unable to transcribe double stranded DNA templates in vitro. See Broyles et al., *J. Biol. Chem.* 263: 10745–60 (1988). The factor is a heterodimer consisting of a 77kDa polypeptide and a 82kDa polypeptide, which are respectively encoded by the D6R and A8L gene orf of the vaccinia WR genome. See Gershon and Moss, *Proc. Nat'l Acad. Sci. USA* 87: 4401–05 (1990). VETF proteins are expressed late in infection and packaged into the nascent virus particles. A defective virus lacking the D6R or the A8L gene isolated from VETF expressing cells should therefore be able to perform one more complete life cycle on a non-complementing cell line without further limitations of protein synthesis.

Protein synthesis is an essential requirement for the use of such defective viruses as "abortive infection vaccines". Such vaccines include avipoxviruses expressing foreign genes that used to immunize mammalian hosts. In the mammalian host, the viruses do not multiply, but rather undergo an abortive life cycle. Nevertheless, this type of vaccine stimulates immune response of particular T-cells. See Taylor and Paoletti, supra. A defective virus lacking VETF is desirable because it should be able to perform an additional life cycle in wild-type hosts as compared to viruses capable only of performing abortive life cycles.

Another gene chosen for complementation of defective virus is the J1R gene that is essential for virus growth in tissue culture. Although its gene product has not been identified so far, this orf is of considerable interest due to its location adjacent to the thymidine kinase gene on the vaccinia virus genome. Deletion of a sequence that includes the orf J1R and at least parts of the adjacent thymidine kinase gene (J2R) results in a virus which is dependent on a complementing cell line and which is at the same time selectable by negative selection on tk-negative cells such as LM(TK$^-$) cells and human 143 B osteosarcoma cells. Using this additional selection procedure, pure stocks of defective virus are rapidly obtained.

Defective poxviruses of the present invention can be produced with many of the same methods used to construct recombinant viruses having inserts in non-essential regions. For example, in vivo recombination via homologous flanking region can be used. See Panicali and Paoletti, *Proc. Nat'l Acad. Sci. USA* 79: 4927–31 (1982); Mackett et al., *Proc. Nat'l Acad. Sci. USA* 79: 7415–19 (1982)). A preferred method of producing defective poxviruses is direct molecular cloning and heterologous packaging. See U.S. Pat. No. 5,445,953; U.S. application Ser. No. 07/914,738; Scheiflinger et al., *Proc. Nat'l Acad. Sci. USA,* 89: 9977–81 (1992); Merchlinsky and Moss, *Virol.* 190: 522–26 (1992)).

A defective poxvirus with unique restriction site(s) either in the essential gene or in the former location of the essential gene may be used as a cloning vehicle. The vector arms of the parental virus having its unique site in an essential region may be ligated with the foreign gene and packaged in the complementing cell line with fowlpox virus ("FPV") as helper virus. Since FPV cannot multiply in mammalian cells, this virus plays no further role as contaminant in the plaque assays that follow. Re-ligated defective virus without insert may still form plaques. Careful preparation of vector arms and forced cloning of the insert into the virus will solve this problem, however.

Pharmaceutically acceptable carriers for use with the invention include aqueous solutions, non-toxic excipients, including salts, preservatives, buffers and the like, as described in REMINGTON'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (7th ed.).

The present invention is further illustrated by the following non-limiting examples.

EXAMPLE 1
Construction of a Defective Vaccinia Virus Lacking the I7L-protein ("d-I7L-ZG") and a Complementing Cell Line Based on Mouse L-M(TK⁻)-cells ("L-I7L")

Construction of Complementing Cell Line L-I7L

The first step in the construction of the helper cell line is cloning of the 17L-orf by PCR-mediated techniques into an E. coli expression plasmid and into an eukaryotic expression plasmid. Expression of the orf in E. coli allows rapid production of the protein for immunization of rabbits to obtain anti-I7L-protein antibodies that are subsequently used to identify the protein in the permanent cell lines.

For this purpose, the I7L-orf is amplified by PCR and the cloned into the plasmid PCRII (InVitrogene, Inc.). The primers oI7-1 (SEQ ID NO:1 (5'-AGT ACT CCA TGG AAA GAT ATA CAG ATT TAG-3') and oI7-2 (SEQ ID NO:2) (5'-ATC CCG GGT TTT AGA GAC TTT GAA GCT ACT-3') are used to amplify the I7L-gene as a 1.3 kb fragment. This fragment is inserted in the plasmid pCRII, which results in pCR-I7L.

Plasmid pCR-I7L is the source of the NcoI-SmaI gene fragment that is inserted by forced cloning into the plasmid pUCAS1, a derivative of pUC19. See Yanish-Perron et al., Gene 33(I): 103–119 (1985). Plasmid pUCAS1 harbors three appropriate restriction sites (RcaI, NcoI, SphI) in a row with an ATG trinucleotide in-frame to the open reading frame of the pUC19 lacZ portion. This construction allows over expression of the 17L-orf downstream of the E. coli lacZ promoter. See FIG. 1. Plasmid pUCAS1 can be created by the following steps: first, vector pUC8417 lacking the lac promotor is constructed via PCR. The plasmid pUC19 is amplified using the synthetic oligonucleotides pPCR2020 and pPCR1697. The resulting 2300 bp long PCR product is blunt ended with S1 nuclease and circularized with T4 DNA ligase. Second, the lacZ promotor region of pUC19 is amplified using the primers pPCR 1927 and pPCR1902 and inserted into pUC8417 as a BglII-NcoI fragment creating the 2522 bp long PUCAS1.

Plasmid pUCAS1 can be cleaved with BbsI, a type III restriction enzyme that cuts in the RcaI site in the same way as RcaI does, which creates a 5'-CATG NcoI compatible overhang. This construction allows exact excision of a cloned gene of interest at its ATG without any requirements for the nucleotide sequence of its second condon. Primer used for construction of pUCAS1 are described below.

Sequences of PCR primers used for the construction of pUCAS1

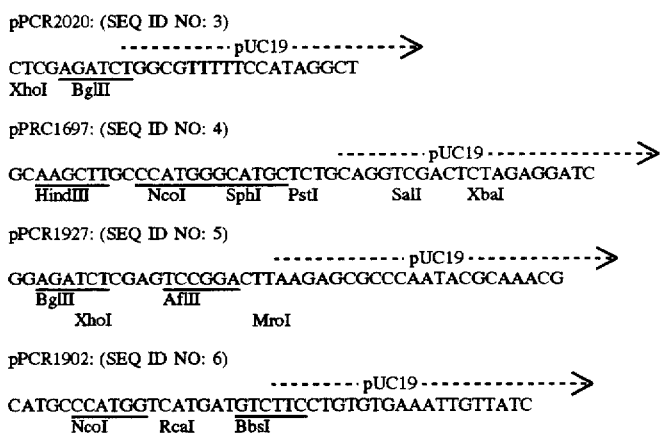

```
pPCR2020: (SEQ ID NO: 3)
                ----------pUC19---------->
CTCGAGATCTGGCGTTTTTCCATAGGCT
XhoI  BglII pPRC1697: (SEQ ID NO: 4)
                        ---------pUC19-------------->
GCAAGCTTGCCCATGGGCATGCTCTGCAGGTCGACTCTAGAGGATC
  HindIII   NcoI   SphI  PstI      SalI    XbaI pPCR1927: (SEQ ID NO: 5)
                    ------------pUC19------------>
GGAGATCTCGAGTCCGGACTTAAGAGCGCCCAATACGCAAACG
  BglII     AflII
  XhoI            MroI pPCR1902: (SEQ ID NO: 6)
              --------pUC19-------------->
CATGCCCATGGTCATGATGTCTTCCTGTGTGAAATTGTTATC
  NcoI   RcaI  BbsI
```

To obtain gene fragment for insertion, the NcoI site around the ATG of the I7L-orf (introduced by primer oI7-1) and the SmaI site (present in the primer region of oI7-2) are used in cleaving pCR-I7L. The 1.3 kb fragment is then inserted into the modified pUC19 plasmid PUCASI, which is cut with NcoI and SmaI, which results in the plasmid pUCAS-I7L.

The I7L-protein is expressed in E. coli cells (strain JM105) harboring the plasmid pUCAS-I7L. Over expression of the protein is obtained by induction of the lac-promoter with the chemical IPTG. Bacterial lysates are subjected to polyacrylamide gel electrophoresis and the I7L-protein band is excised from the gel. Rabbits are immunized with the eluted material and complete Freund's adjuvant (30 micrograms of protein per dose, s.e. and i.m.). After one month, the animals are boosted with the same dose in incomplete Freund's adjuvant and development of antibodies is monitored by Western blots.

The Western blots are performed essentially as described by Towbin et al., *Proc. Nat'l Acad. Sci.* USA 76: 4350–54 (1979). The first antibody is a rabbit anti-I7L antibody (see above) used in a 1:100 dilution. The second antibody is a goat-anti-rabbit IgG coupled with alkaline phosphatase (BioRad, Inc.) used in a 1:1000 dilution. The reagents (BCIP and NBT) and staining protocols are from Promega, Inc.

Figure 2:
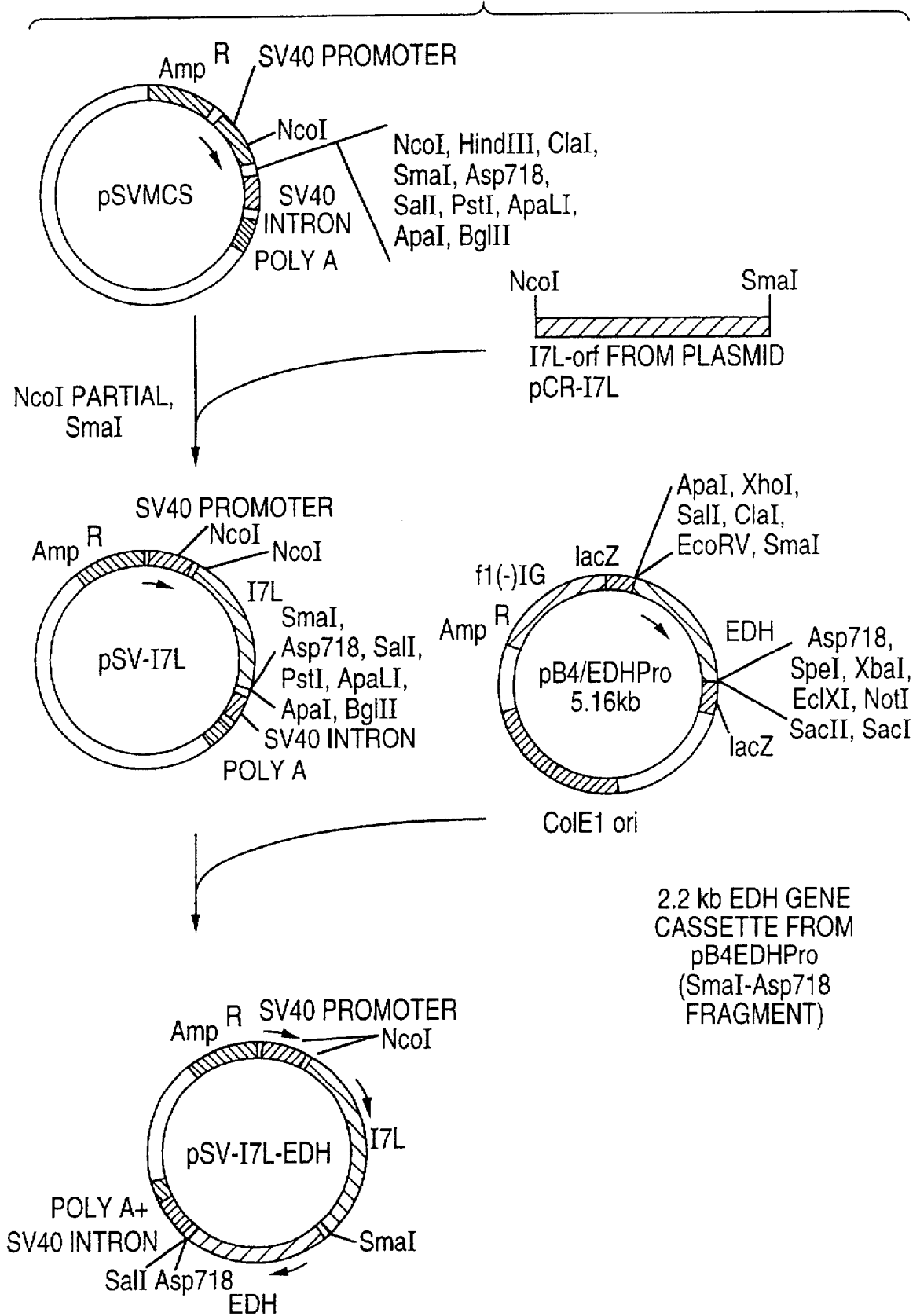
FIG. 2 schematically depicts the construction of plasmid pSV-I7L-EDH.

The same NcoI-SmaI gene fragment used for bacterial expression is part of the expression plasmid pSV-I7L-EDH See FIG. 2. A gene cassette including an internal ribosomal entry site, the dihydrofolate reductase ("dhfr") and hygromycin ("hph") genes form the "EDH gene cassette," which is inserted as a SmaI-Asp718 fragment between the unique restriction sites SmaI and Asp718 of the plasmid pSV-I7L. This construction yields plasmid pSV-I7L-EDH. Plasmid pSV-I7L is obtained by inserting the 1.3 kb NcoI-SmaI fragment of pCR-I7L is inserted between the NcoI-SmaI of plasmid pSVNco/MCS. The plasmid pSVNco/MCS is a derivative of pSVβ (Clontech, Inc.) having substituted the lacZ gene with a series of multiple, unique cloning sites. See FIG. 2.

To obtain pSV-MCS, pSVβ was digested with NotI, deleting the β-galactosidase gene and religated. The resulting plasmid was digested with SalI and HindIII, filled with Polymerase K and religated. This step resulted in the deletion of the MCS 3' of the polyadenlyation site. The plasmid pSVNco/MCS is constructed by digesting plasmid pSV-MCS with XhoI and relegation with a linker destroying the XhoI site. The linker contained sites for the restriction endonuclease NcoI, HindIII, ClaI, SmaI, EcoRI, Asp718, KpnI, SalI, PstI, ApaLI, ApaI and BglII and is characterized by the sequence (SEQ ID NO: 7) 5'-TCG ACC ATG GAC AAG CTT ATC GAT CCC GGG AAT TCG GTA CCG TCG ACC TGC AGG TGC ACG GGC CCA GAT CTG ACT GAC TGA-3'.

In pSV-I7L-EDH, described above, the I7L-orf is controlled by the SV40 early promoter. The selection marker for obtaining permanent cell lines is a fusion gene including the dhfr and hph genes, which allows efficient screening and amplification of genes of interest in permanent cell lines.

This plasmid is transfected into mouse L-M($TK^-$) cells. Mouse L-M($TK^-$) cells (ATCC CCL1.3) were obtained from the American Type Culture Collection (Rockville, Md.). The cells are transfected with the plasmid pSV-I7L-EDH according to Graham and van der Eb, supra and incubated in selective medium based on hygromycin B (DMEM, 10% fetal bovine serum, 200 mg/ml hygromycin B). After 10–14 days, colonies become visible. These colonies are expanded, subcloned twice and then characterized further. Permanent hph positive cell lines are selected in the presence of the hygromycin B. Western blots are used to show that the gene of interest, the I7L-protein is expressed. The cell lines expressing the highest levels of I7L-protein are further characterized by Southern blotting and used as the complementing cell line and named L-I7L.

Construction of Defective Virus d-I7L-ZG

Figure 3:
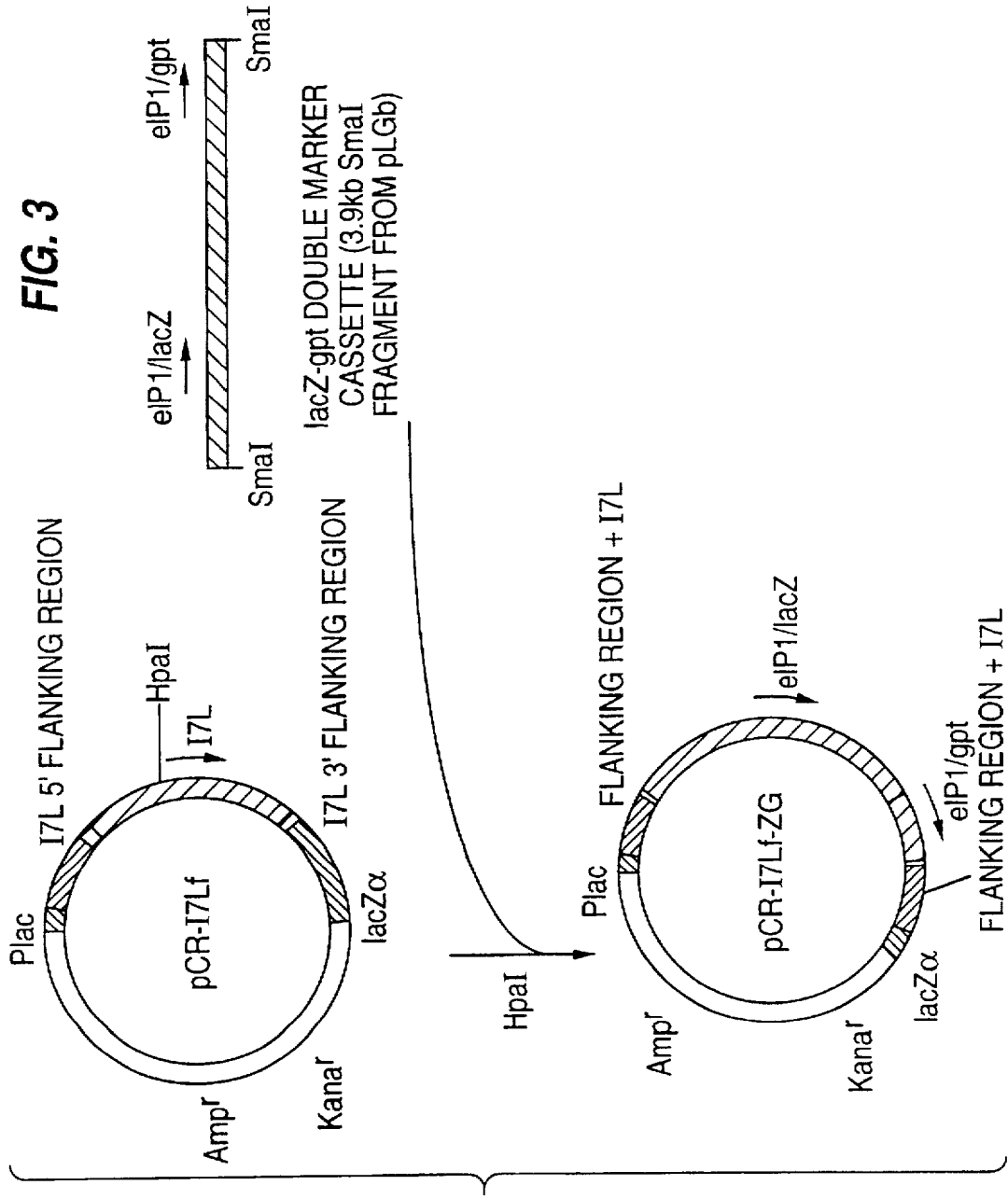
FIG. 3 schematically depicts the construction of plasmid pCR-I7Lf-ZG.

To construct the virus d-I7L-ZG, the plasmid pCR-I7Lf is constructed as summarized in FIG. 3. This plasmid is based on the pCRII vector and contains the I7L-orf, including about 0.5 kb of flanking region on either side. The primers oI7-3 (SEQ ID NO:8) (5'-AGG AGT TAA TGA GGC CAA TGG A-3') and oI7-4 (SEQ ID NO:9) (5'-GAC ATA GGT ATA GAA TCC GGA-3') are used to obtain a PCR product of about 2.3 kb that is subcloned into the PCRII plasmid to yield pCR-I7Lf.

A double gene cassette including the *E. coli* genes lacZ and gpt is excised as a SmaI fragment from the plasmid pLGb and inserted into the unique HpaI site located within the I7L-orf, which inactivates the pCR-I7L gene in the resulting plasmid pCR-I7Lf-ZG.

Plasmid pLGb is obtained from p2T, which is based on plasmid p1Ta and pTZ19R (Pharmacia). First, the large PvuII vector fragment of pTZ19R is ligated with annealed oligonucleotides P-1T(1): (SEQ ID NO:10) 5'- AGT TTA AAC GGC GCG CCC GGG CTC GAG AGG CCT CTG CAG ATG CAT CCA TGG GGA TCC GAA TTC-3' and P-1T(2) (SEQ ID NO:11): 5'-GAA TTC GGA TCC CCA TGG ATG CAT CTG CAG AGG CCT CTC GAG CCC GGG CGC GCC GTT TAA ACT-3'. This yields plTa, which is then cleaved with EcoR1 and BamH1. The cleaved plTa is then ligated to annealed oligonucleotides P-2T(1) (SEQ ID NO:12): 5'-GAT CCT ACG TAT CTA GAA TTA ATT AAT GGC CAA TTT AAA TGC CCG GGA-3' and P-2T(2) (SEQ ID NO:13): 5'-AAT TTC CCG GGC ATT TAA ATT GGC CAT TAA TTA ATT CTA GAT ACG TAG-3' This yields plasmid p2T, which is then cleaved with SmaI. A double gene cassette including the *E. coli* genes lacZ and gpt is inserted as a HindIII, SalI and Klenow polymerase treated fragment. The double gene cassette is obtained from the plasmid pZgpt-a, which is based on plasmid pTNa and related plasmids.

For the construction of the d-I7L-ZG virus, plasmid pCR-I7Lf-ZG is inserted into the WR strain vaccinia virus by in vivo recombination in CV-1 cells. First, $5\times10^6$ CV-1 cells are infected with 0.1 pfu/cell of vaccinia WR, grown for 1 hour, transfected with a calcium phosphate precipitate that includes 20 micrograms of the plasmid pCR-I7Lf-ZG, and then grown for 3 days. See Graham and van der Eb, *Virol.* 179: 247–66 (1973). A viral crude stock is prepared and used for plaque assays on L-I7L-cells in the presence of gpt selection, Falkner and Moss, *J. Virol.* 62: 1849–54 (1988), and blue plaque screening, Chakrabarti et al., *Mol. Cell. Biol.* 5: 3403–09 (1985).

The defective virus grows in L-I7L cells only and is gpt and lacZ positive, while the wild-type virus grows in both cell lines, but is gpt and lacZ negative. The purification is performed five times. The purified defective viruses are then grown to larger scale and examined by Southern blotting. The absence of wild-type virus and presence of the predicted bands confirms that the correct defective genomes have formed. Plaque assays of the defective viruses on the complementing cells and on wild-type cells confirm that the host range of the defective viruses are limited to the complementing cell line. Animal studies confirm that the defective viruses are non-pathogenic.

Figure 4:
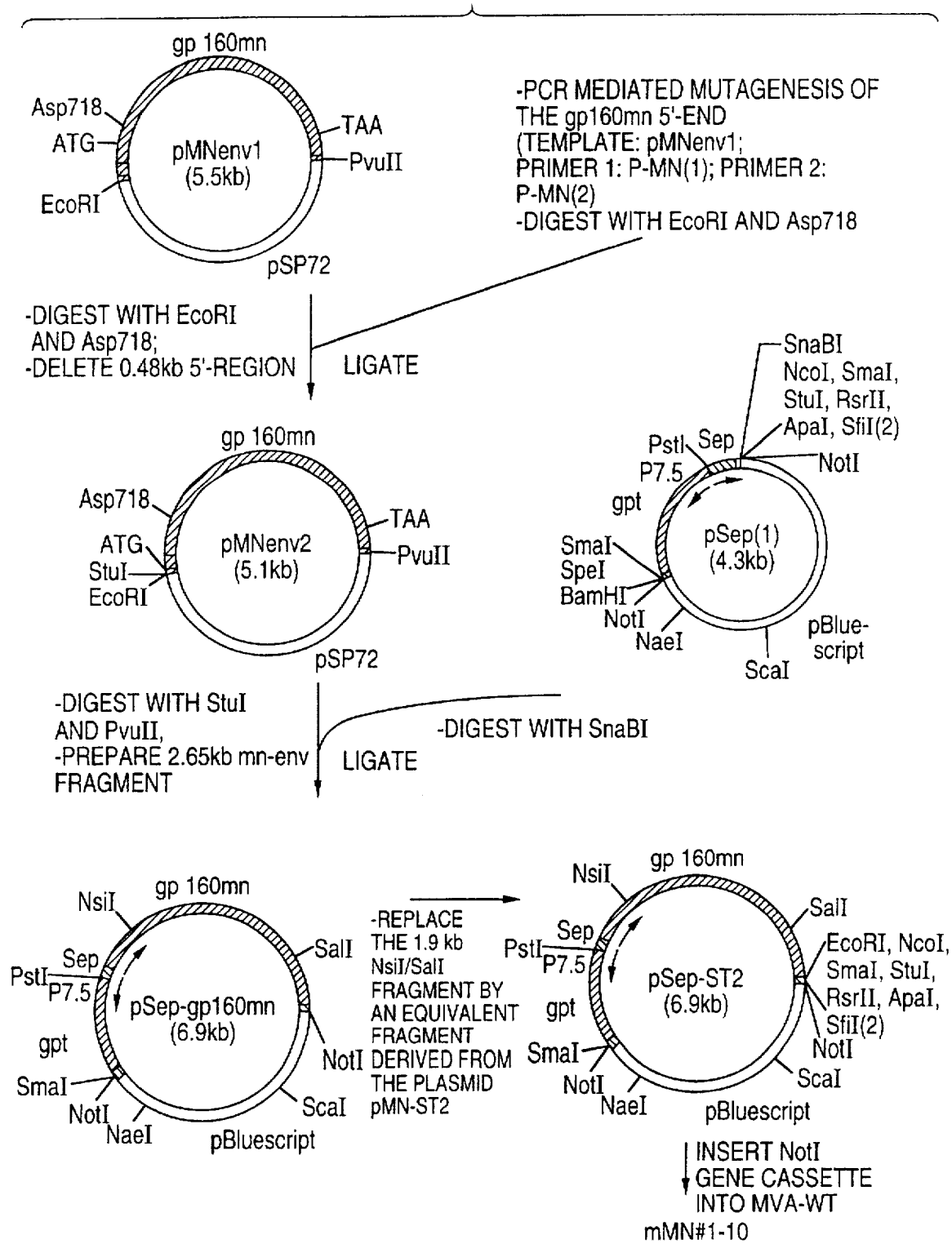
FIG. 4 schematically depicts the construction of plasmid pSep-ST2.

EXAMPLE 2

Construction of a Defective Vaccinia Virus Expressing the HIV env gp160 Gene (d-I7L-MN) in the Complementing Cell Line L-I7L To demonstrate foreign gene expression in the novel system, the HIV gp160 gene of the HIV MN strain is inserted into the essential region I7L. For this purpose, a gene cassette from a SmaI fragment of plasmid pSep-ST2 is obtained.

Plasmid pSep-ST2 contains the HIV-1 gp160MN sequences controlled by the strong semi-synthetic poxvirus promoter Sep and a selection cassette that includes the P7.5 gpt gene. See Falkner and Moss, *J. Virol.* 62: 1849–54 (1988). The construction of pSep-ST2 is depicted schematically in FIG. 4. To construct plasmid pSep-ST2, plasmid pMNenv2 is created from pMNenv1 (M. Reitz, N.C.I., Bethesda, Md.) and a PCR-mediated mutated segment of gp160 mn.

The cassette from pSep-ST2 contains the HIV gp160gene and *E. coli* gpt gene, and is inserted into the unique HpaI site of pCR-I7Lf (FIG. 3) resulting in the plasmid pCR-I7Lf-MN. This plasmid is used in an in vivo recombination experiment in CV-1 cells involving WR wild-type virus to obtain a viral crude stock consisting of a mixture of defective viruses (having performed both cross-over events to become a regular recombinant virus), viruses having performed only one cross-over event and a wild-type helper viruses. An overall explanation of cross-over events is contained in Falkner and Moss, *J. Virol.* 64: 3108–3111 (1990). This mixture of viruses is plaque purified in the complementing cell line L-I7L and checked for purity as described in Example 1, except that the plaque assays are based solely on gpt-selection. The resulting virus is designated d-I7L-MN and used for expression of recombinant gp160in L-17L cells.

The virus d-17L-MN is used in combination with its complementing cell line to express gp160. L-17L-cells are infected with 0.1 pfu of d-17L-MN and grown for three days. The recombinant protein is detected by Western blots using an anti-gp41 monoclonal antibody in a method according to Towbin et al., supra.

Animal experiments in mice are carried out to demonstrate that d-I7L-MN is non-pathogenic but still able to prime the immune response.

EXAMPLE 3

Construction of a Defective Vaccinia Virus Lacking the Early Transcription Factor Large Subunit (d-A8L-ZG) and of a Complementing Cell Line Construction of a Helper Cell Line Based on Mouse L-M (TK⁻) Cells (L-A8L)

The VETF factor is a heterodimer comprised of a 77 kD polypeptide and a 82 kD polypeptide, which are encoded respectively by the D6R and the A8L orfs of the VV-WR genome. Gershon and Moss, *Proc. Nat'l Acad. Sci.* USA 87: 4401–05 (1990). VETF proteins are expressed late in infection and packaged into the nascent virus particles. A defective virus lacking VETF is desirable because it should be able to perform an additional life cycle in wild-type hosts as compared to viruses capable only of performing abortive life cycles.

The D6R subunit contains a possible ATP binding site and has been found to bind to the early promotor DNA sequence. See Broyles and Li, *J. Virol.* 67: 5677–80 (1993). In order to avoid undesirable protein-DNA interactions in the complementing cell line the A8L orf has been chosen.

The first step in the construction of the helper cell line is cloning of the A8L orf by PCR mediated techniques into an *E. coli* expression plasmid and into an eukaryotic expression plasmid. Expression of the orf in *E. coli* allows rapid production of the protein for immunization of rabbits to obtain anti-VETF large subunit antibodies that are subsequently used to identify the protein in the permanent cell lines.

For this purpose, the A8L-orf is amplified by PCR and the cloned into the plasmid pCRII. The primers oA8-1 (SEQ ID NO:14)(5'-CTG CAG ATG CGA TAT ATA GTA AGT CCG CA-3') and oA8-2 (SEQ ID NO:15)(5'-ACC CGG GTT TAA TTT ATT TGT GCT CTT C-3') are used to amplify the A8L-gene as a 2.1 kb fragment. This fragment is inserted into the plasmid pCRII (InVitrogen Inc.) resulting in pCR-A8L.

Figure 5:
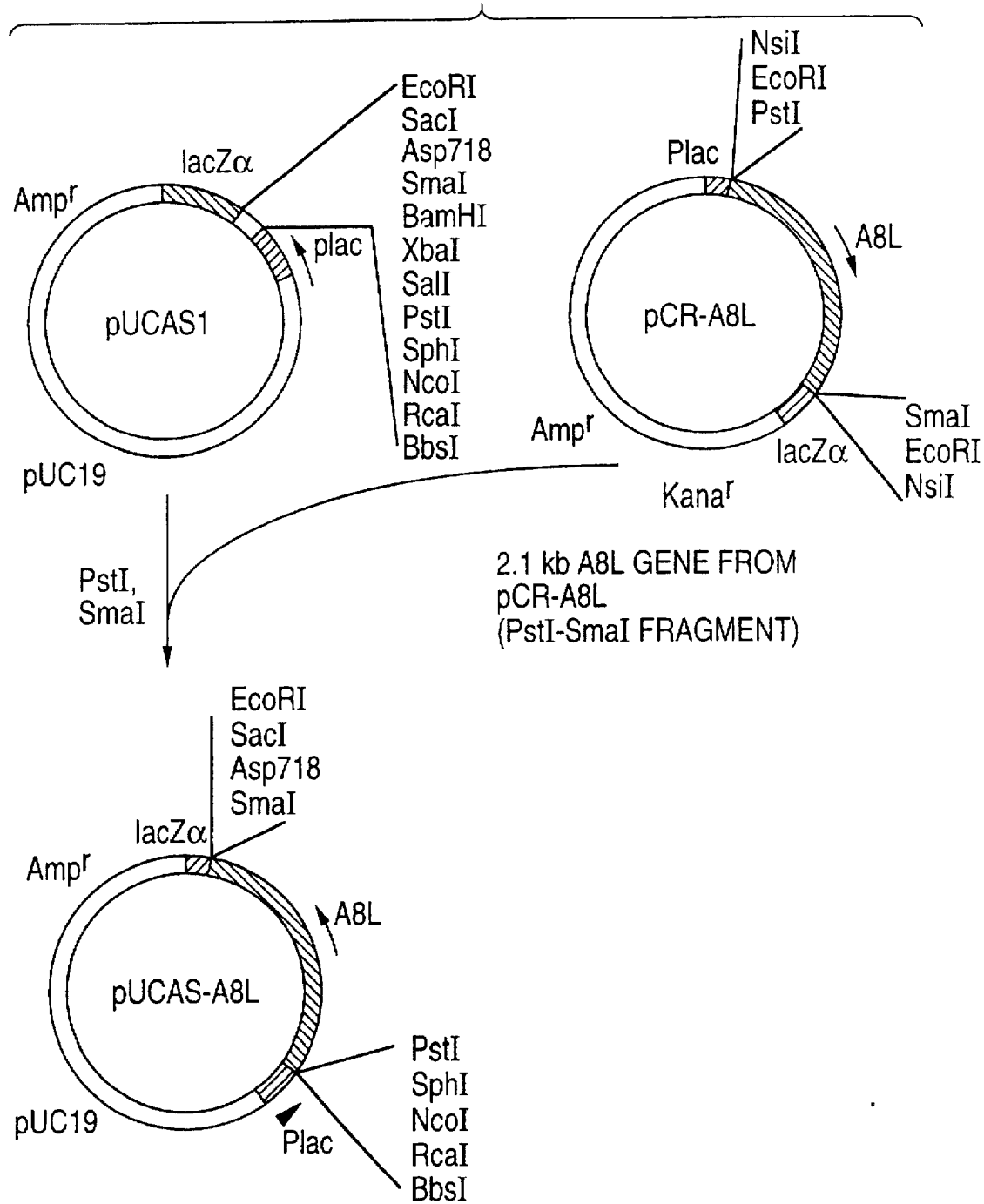
FIG. 5 schematically depicts the construction of plasmid pUCAS-A8L.

Plasmid pCR-A8L is the source of a 2.1 kb PstI-SmaI gene fragment. The PstI site upstream of the ATG of the A8L-orf (introduced by primer oA8-1) and the SmaI site (introduced by primer oA8-2) are cleaved to obtain the fragment. The fragment is inserted by forced cloning into the plasmid pUCASI, a derivative of pUC19 as described above, and allows over expression of the A8L-orf downstream of the *E. coli* lacZ promoter. See FIG. 5. This insertion results in the plasmid pUCAS-A8L.

Expression of the VETF large subunit protein is obtained after induction of the bacteria by IPTG. Bacterial lysates are the source for the isolation of the protein by standard techniques. The A8L-protein is expressed in *E. coli* cells (strain JM105) harboring the plasmid pUCAS-A8L. Over expression of the protein is obtained by induction of the lac-promoter with the chemical IPTG. Bacterial lysates are subjected to polyacrylamide gel electrophoresis and the A8L-protein band is excised from the gel. Rabbits are immunized with the eluted material and complete Freund's adjuvant (30 micrograms of protein per dose, s.c. and i.m.). After one month, the animals are boosted with the same dose and development of antibodies is monitored by Western blots.

Proteins are detected by Western blots. The Western blots are done essentially as described by Towbin et al., supra. The first antibody is a rabbit anti-A8L protein antibody used in a 1:100 dilution. The second antibody is a goat-anti-rabbit IgG coupled with alkaline phosphatase (BioRad, Inc.) used in a 1:1000 dilution. The reagents (BCIP and NBT) and staining protocols are from Promega, Inc.

Figure 6:
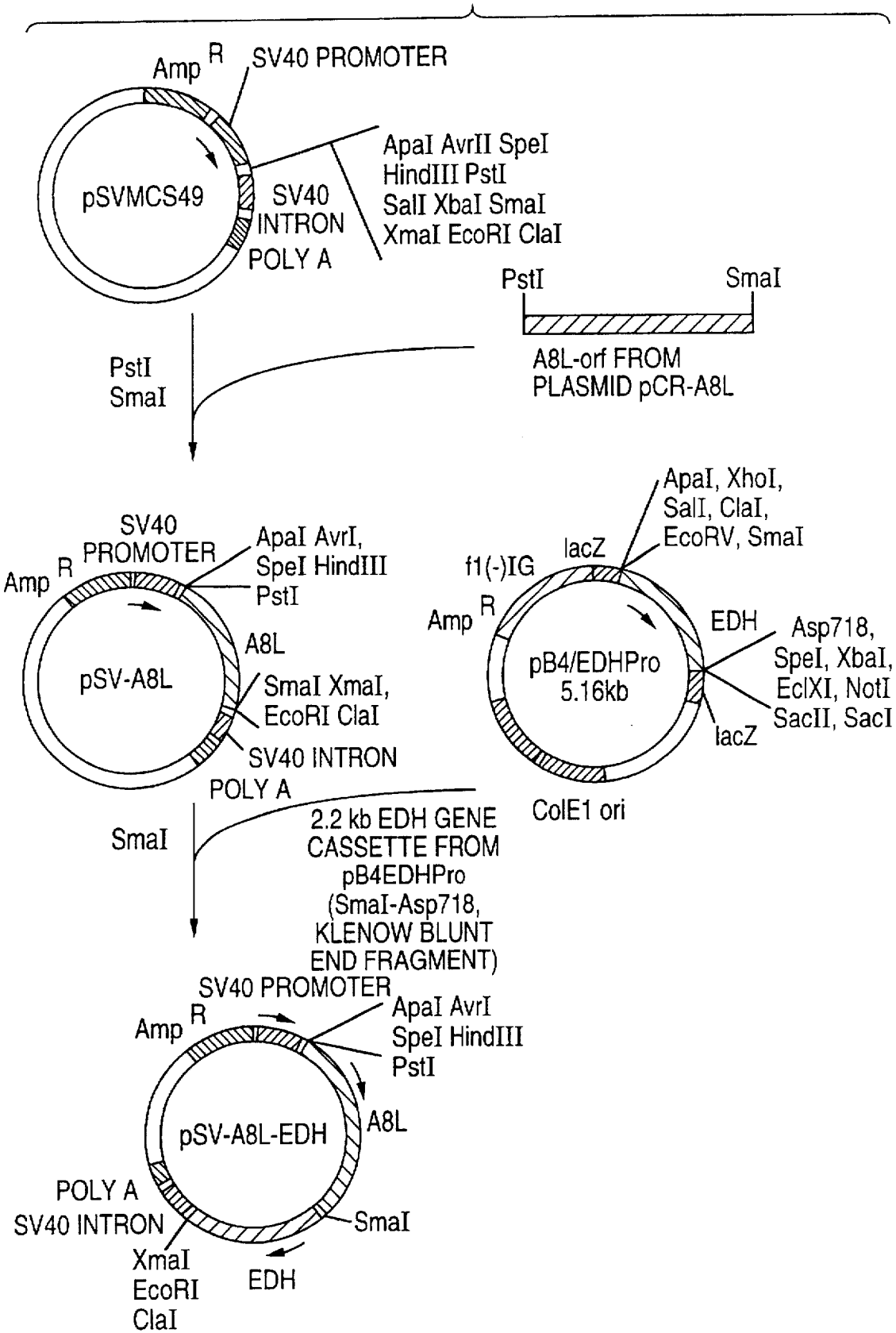
FIG. 6 schematically depicts the construction of plasmid pSV-A8L-EDH.

The same PstI-SmaI gene fragment used for bacterial expression is part of the expression plasmid pSV-A8L-EDH. See FIG. 6. The 2.1 kb PstI-SmaI fragment of pCR-A8L is inserted between the PstI-SmaI sites of plasmid pSVNco/MCS resulting in pSV-A8L. A gene cassette consisting of an internal ribosomal entry site, the dhfr and hph genes (SmaI-Asp718 and Klenow-treated EDH gene cassette) is inserted into the unique restriction site SmaI of the plasmid pSV-A8L, yielding plasmid pSV-A8L-EDH.

In plasmid pSV-A8L-EDH, the A8L-orf is controlled by the SV40 early promoter. The selection marker for obtaining permanent cell lines is a fusion gene consisting of the dhfr gene and the hph gene as described in Example 1.

The plasmid pSV-A8L-EDH is transfected into Mouse L-M (TK⁻) cells (ATCC CCL1.3) in a method according to Graham & van der Eb, supra and incubated in selective medium (DMEM, 10% fetal bovine serum, 200 micrograms/ml hygromycin) and further treated as described in Example 1. Permanent hygromycin phosphotransferase positive cell lines are selected in the presence of the antibiotic hygromycin B. Western blots are used to determine whether the gene of interest, the VETF large subunit, is expressed. The cell lines expressing the highest levels of VETF large subunit is further characterized by Southern blotting and used as the complementing cell line and named L-A8L.

Construction of the Defective Virus d-A8L-ZG

Figure 7:
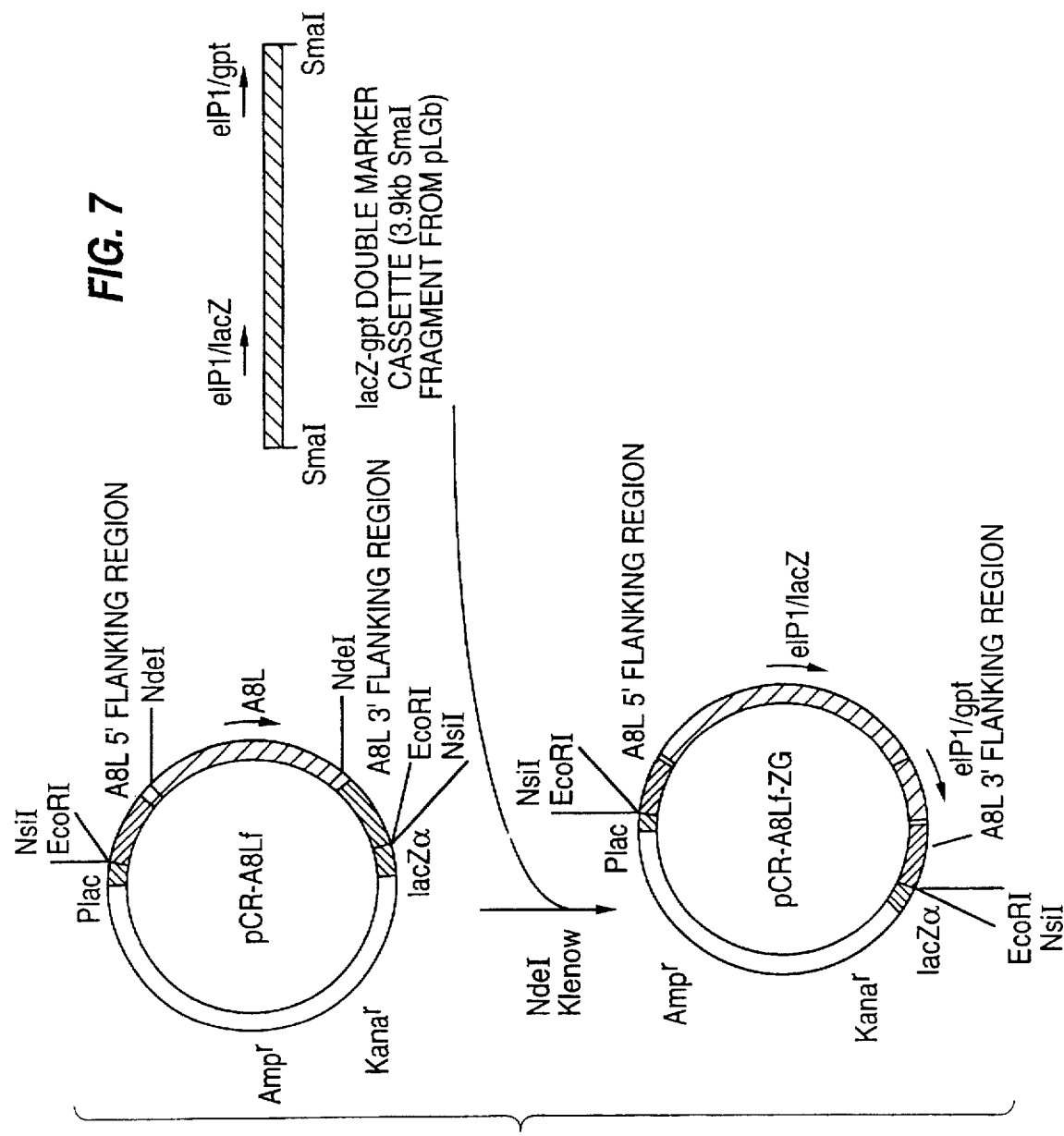
FIG. 7 schematically depicts the construction of plasmid pCR-A8Lf-ZG.

To construct the virus d-A8L-ZG, plasmid pCR-A8Lf is constructed as schematically shown in FIG. 7. This plasmid is based on the pCRII vector and contains the A8L-orf including about 0.5 kb of flanking region on either side. The primers oA8-3 (SEQ ID NO:16) (5'-TTC AGA TAA TGA ACT TAC CA-3') and oA8-4 (SEQ ID NO: 17) (5'-TTG GAG AAC TTG ATA CGC CG-3') are used to obtain a PCR product of about 3.3 kb that is subcloned into the PCRII plasmid to yield pCR-A8Lf.

A double gene cassette containing the E. coli genes lacZ and gpt is excised as a SmaI fragment from the plasmid pLGb (see Example 1) and inserted between the two NdeI sites present at the 5' and at the 3' end of the A8L-orf of the plasmid PCR-A8Lf, resulting in pCR-A8Lf-ZG. In the course of this insertion almost the whole A8L orf is removed except 80 bp at its 5' end and 80bp at its 3' end. This strategy deletes the essential region from the defective poxvirus and, therefore, makes it practically impossible for the virus to rescue the essential region contained in the complementing cell line.

For the construction of the d-A8L-ZG virus the plasmid pCR-A8L-ZG is inserted into the vaccinia virus WR. The plasmid pCR-A8Lf-ZG is used for in vivo recombination in CV-1 cells. First, $5 \times 10^6$ CV-1 cells are infected with 0.1 pfu/cell of vaccinia WR, incubated for 1 hour, transfected with a calcium phosphate precipitate (according to Graham & van der Eb, supra) containing 20 micrograms of the plasmid pCR-A8L-ZG and grown for 3 days. This results in a crude stock containing wild-type (helper viruses) and defective viruses. To obtain pure stocks of the defective virus, plaque assays are carried out in L-A8L-cells that are able to complement the defective virus. The viral crude stock is prepared and used for plaque assays on L-A8L-cells in the presence of gpt selection (Falkner and Moss, supra (1988) and blue plaque screening (Chakrabarti et al., supra). The plaque purification is repeated five times. The purified defective poxviruses are grown to larger scale and examined by Southern blotting. The absence of wild-type virus and presence of the predicted bands confirms that the correct defective genomes have formed. Plaque assays of the defective viruses on the complementing cells and on wild-type cells confirm that the host range of the defective viruses are limited to the complementing cell line. Animal studies confirm that the defective viruses are non-pathogenic.

EXAMPLE 4

Construction of a Defective Vaccinia Virus Expressing the HIV env gp160CM Gene (d-A8L-CM) in the Complementing Cell Line L-17L by Reverse gpt-Selection As outlined in the general description above, a poxvirus that is gpt-positive can receive a foreign DNA insert. This approach has an important advantage, namely the opportunity of using reverse gpt selection to obtain, fast and efficient, pure stocks of defective virus.

To demonstrate foreign gene expression in the novel system the HIV-1 gp160gene of the HIV CM235 strain is inserted into the essential region A8L. A gene cassette for this purpose is obtained from the plasmid pSep-envCM. Plasmid pSep-envCM is derived from plasmid pCMenv. Plasmid pCM-envCM contains the gp160gene of the virus CM235 cloned as an EcoRI-SalI fragment into the bluescript vector (Stratagene, Inc.) and was obtained from F. McCutchan, Henry M. Jackson Foundation, Rockville, Md.). Plasmid pCM-envCM is cut with SmaI and ApaI and inserted between the SnaBI and ApaI sites of pSep(1), which yields pSep-envCM.

The gene cassette having HIV gp160CM gene controlled by the Sep promoter (obtained as a NotI fragment from the plasmid pSep-envCM) is inserted between the NdeI sites of pCR-A8Lf, which yields plasmid pCR-A8Lf-CM. The plasmid pCR-A8Lf-CM is used for transfection into L-A8L cells infected with the virus d-A8L-ZG, which is gpt and lacZ positive. First, $5 \times 10^6$ L-A8L cells are infected with 0.1 pfu/cell of d-A8L-ZG (see Example 3), grown for 1 hour, transfected with a calcium phosphate precipitate (according to Graham and van der Eb, supra) having 20 micrograms of the plasmid pCR-A8Lf-CM and grown without selection for 3 days. A viral crude stock is prepared and used for plaque assays on L-A8L-cells in the presence of 6-thioguanine, which is a condition for reverse gpt-selections See Isaacs et al., supra. The plaque purification of white plaques using blue plaque screening conditions (according to Chakrabarti et al., supra) is repeated five times. The progeny plaques have a white phenotype, are gpt-negative and have integrated the gp160CM gene. Southern and Western blots respectively confirm the structure and expression of the foreign gene by the virus. A virus isolate with the correct structure is named d-A8L-CM. Animal studies in rabbits and mice confirm that the virus is non-pathogenic, but does induce an immune response against gp160CM.

EXAMPLE 5

Screening Poxvirus Essential Genes for suitability as Complementing Agents

Most poxviruses have been extensively characterized, and the nature of the gene products encoded by the poxvirus genome is known. For example, vaccinia contains over 260 open reading frames (ORFs) coding for 65 or more amino acids in vaccinia Over 180 vaccinia ORFs have been characterized as being essential or non-essential. See Johnson et al., Virol. 196: 381–401 (1993). About 70 non-essential ORFs have been identified by deletion and insertion analyses. About 14 essential genes and 24 temperature sensitive (ts) mutants are described in Table 1 of Johnson et al., supra. Ts mutants are conditionally lethal and the affected ORFs therefore belong to the essential regions. Therefore, about 38 essential genes are known. The function of many other vaccinia genes is however, unknown. A good estimate is that 50–70% of the vaccinia genes are essential. Accordingly, there exists a number of candidate essential genes that may be useful as complementing agents.

To determine whether a given poxvirus essential gene is suitable as a complementing agent, certain parameters were initially set. First, the molecular weight of the essential gene product preferably should be about 50 kilodaltons or less, and the gene product should be soluble in a host cell cytoplasm, where the entirety of the poxvirus life cycle takes place. Compliance with these parameters should yield candidate essential genes that possess a reasonable probability of stable expression and accumulation of the gene product. Candidate genes were then cloned into appropriate expression plasmids and transfected into two orthopoxvirus host cell lines, namely Vero cells (African Green Monkey kidney cell line, ATCC CCL 81) and human kidney cell line 293 (ATCC CRL 1573).

Figure 8:
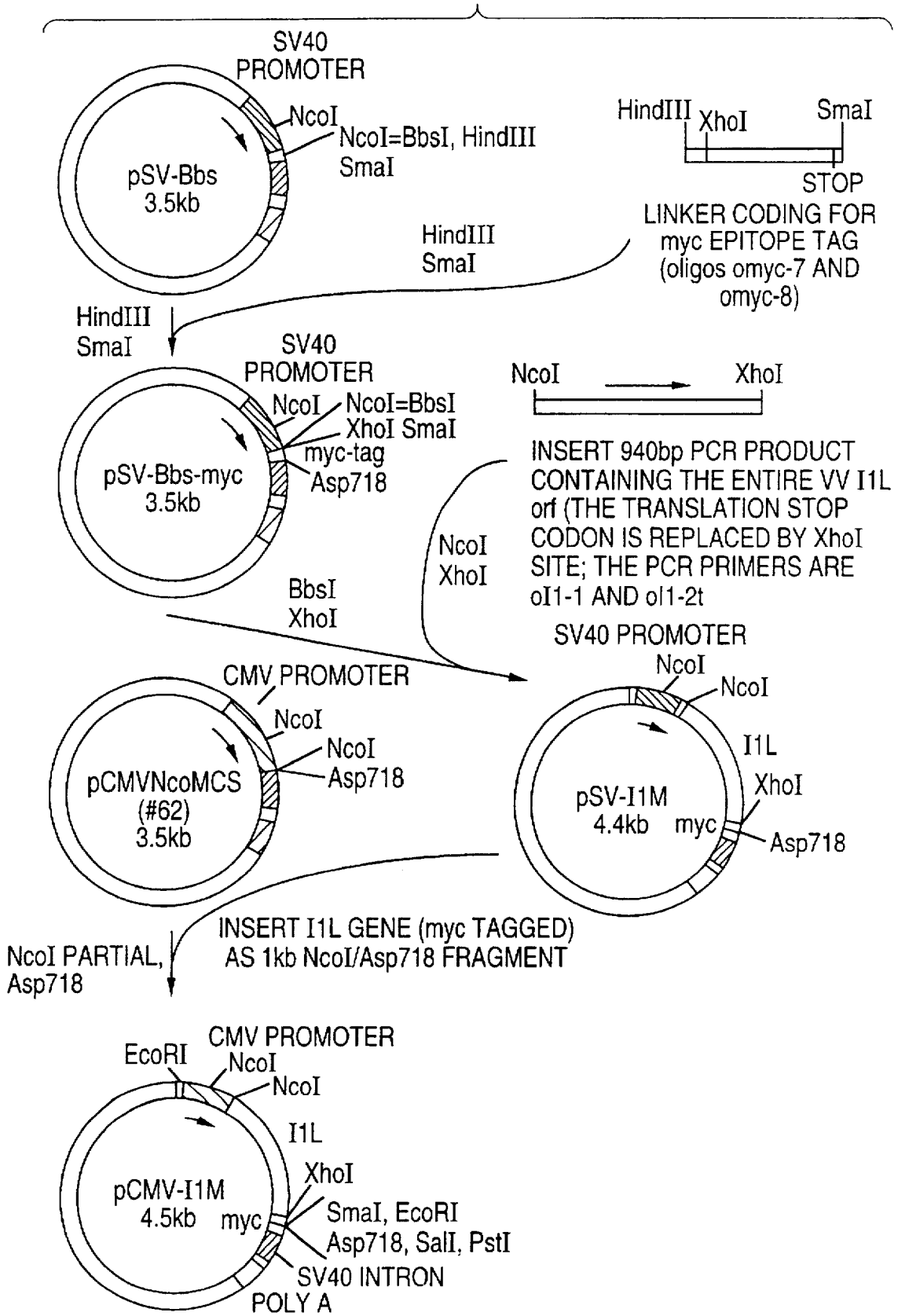
FIG. 8 schematically depicts the construction of plasmid pCMV-I1M, which can be used to evaluate poxvirus genes.

The first step of the screening procedure was the construction of an expression plasmid that contains a eukaryotic CMV-promoter, unique cloning sites and an in-eukaryotic frame epitope of the myc-oncogene. See FIG. 8. The plasmid used to screen the candidate essential genes is referred to as pCMV-I1M, and its construction is described below.

First, plasmid pSV-Bbs was made by cleaving plasmid pSV-MCS with AvrII and HindIII, and substituting the resultant 34bp fragment with the annealed oligonucleotides o58-1 (SEQ ID NO: 18) (5'-CTA GGC TTT TGC AAA AAG CTC CTC GAC CAT GGT GTC TTC AA-3') and o58-2 (SEQ ID NO:19) (5'-AGC TTT GAA GAC ACC ATG GTC GAG GAG CTT TTT GCA AAA GC-3'), which introduces a BbsI site and a NcoI site. Plasmid PSV-MCS was made by digesting pSVβ with NotI, deleting the β-galactosidase gene and followed by religation. The resulting plasmid was digested with XhoI and ligated with a MCS containing the restriction sites for ClaI, EcoRI, SmaI, XbaI, SalI, PstI, HindIII, SpeI, AvrII, ApaI and is characterized by the sequence (SEQ ID NO:20) 5'-CTC GAT AGG GCC CTA GGC CTA CTA GTA CTA AGC TTC TGC AGG TCG ACT CTA GAG GAC CCC GGG GAA TTC AAT CGA TTC GAG-3'.

Next, plasmid pSV-Bbs-myc was made by cleaving plasmid pSV-Bbs with HindIII and SmaI and ligating the cleaved plasmid with the annealed oligonucleotides omyc-7 (SEQ ID NO:21) (5'-AGC TTC TCG AGC TGG AGG AGC AGA AGC TGA TCT CCG AGG AGG ATC TGC TGA GAA AGA GAT AAC CC-3') and omyc-8 (SEQ ID NO:22) (5'-GGG TTA TCT CTT TCT CAG CAG ATC CTC CTC GGA GAT CAG CTT CTG CTC CTC CAG CTC GAG A-3') resulting in the plasmid pSV-Bbs-myc. The myc oligonucleotides code for the myc-tag amino acid sequence (SEQ ID NO:23) LEEQKLISEEDLLRKR.

Plasmid pSV-I1M was then made by obtaining a 940 bp NcoI-XhoI vaccinia fragment by PCR with the primers oI1-1 (SEQ ID NO:24) (5'-GAC TCC ATG GCG GAA TTT GAA GAT CAA CTC-3') and oI1-2t (SEQ ID NO:25) (5'-ATG CCT CGA GTT CAG CAT TAC TTG ATA TAG TA-3'), and inserting this fragment into the BbsI and XhoI cleaved plasmid pSV-Bbs-myc, which results in the vector pSV-I1M.

The myc-tagged I1L gene (termed I1M) was excised as a 1 kb NcoI-Asp718 fragment from plasmid pSV-I1M and inserted into the NcoI (partial)-Asp718 cleaved vector pCM-VNcoMCS resulting in the plasmid pCMV-I1M. Plasmid pCMVNcoMCS was constructed in a manner analogous to pSVNcoMCS except that plasmid pCMVβ(Clontech) was used instead of pSVβ.

To construct the plasmids containing the vaccinia candidate genes, the respective ORFs containing these genes were obtained by PCR. The upstream primers introduced either an NcoI site or a compatible site (see Table 1, "cloning sites" column) and the downstream primers deleted the stop codon of the ORF and introduced either a XhoI or a SalI site (see Table 1 below). The template was DNA of the vaccinia WR strain. The respective ORF fragments were cloned between the NcoI site located downstream of the CMV promoter and the unique XhoI site of pCMV-I1M substituting the I1L gene with the respective vaccinia candidate gene indicated in Table 1.

The insertion of the candidate genes into the expression plasmid creates a fusion gene comprising the vaccinia essential gene and the myc epitope. The genetic constructs encoding the fusion proteins were then transfected into the screening cell lines and expression was detected by Western blots using the myc-tag monoclonal antibody.

The Western blots were done essentially as described by Towbin et al., Proc. Nat'l Acad. Sci. USA 76: 4350–4354 (1979). For analysis of the myc-tagged proteins, the first antibody was the monoclonal antibody myc1-9E10 (Evan et al., Mol. Cell. Biol. 5: 3610–16 (1985)), which is commercially available from Oncogene Science, Inc., NY. The antibody is used in a 1:1000 dilution. The second antibody was a goat-anti mouse IgG coupled with alkaline phosphatase (obtained from Biorad, Inc., cat.#170-6520) used in a 1:1000 dilution. The reagents (BCIP and NBT) and staining protocols were from Promega, Inc.

The results of this screening are shown in Table 1.

TABLE 1

| ORF | size | cloning sites | Vero | 293 | MW exp | MW found |
|---|---|---|---|---|---|---|
| E7L | 502 bp | BsmBI/XhoI | + | + | 21.7 | 24 |
| F11L | 1065 bp | NcoI/XhoI | + | + | 39.7 | 41 |
| E4L | 781 bp | BsmBI/XhoI | + | + | 32.0 | 40 |
| O2L | 327 bp | NcoI/XhoI | − | − | | |
| I1L | 940 bp | NcoI/XhoI | + | + | 38.0 | 40 |
| G2R | 664 bp | NcoI/XhoI | − | − | | |
| G3L | 336 bp | NcoI/XhoI | − | − | | |
| G4L | 375 bp | BbsI/XhoI | − | − | | |
| G5R | 1305 bp | NcoI/SalI | − | − | | |
| G7L | 1116 bp | NcoI/XhoI | − | − | | |
| G8R | 784 bp | NcoI/XhoI | − | − | | |
| J3R | 1003 bp | NcoI/SalI | − | + | 41.1 | 41 |
| J4R | 559 bp | BspHI/XhoI | + | − | 23.5 | 32 |
| H7R | 441 bp | NcoI/XhoI | + | + | 19.1 | 21 |
| D4R | 657 bp | NcoI/XhoI | + | + | 27.3 | 30 |
| D7R | 487 bp | BsmBI/XhoI | − | − | | |
| D9R | 642 bp | NcoI/XhoI | − | − | | |
| D10R | 747 bp | NcoI/XhoI | − | − | | |
| D12R | 865 bp | NcoI/XhoI | − | − | | |
| A1L | 453 bp | NcoI/XhoI | − | − | | |
| A2L | 675 bp | BbsI/XhoI | − | − | | |
| A4L | 847 bp | NcoI/XhoI | − | − | | |
| A6R | 868 bp | BbsI/XhoI | + | + | 35.8 | 32 |
| A18R | 1482 bp | NcoI/XhoI | − | − | | |
| A29L | 919 bp | BsmBI/XhoI | − | − | | |
| B1R | 900 bp | BspHI/XhoI | − | − | | |

About one third of the preselected essential genes could be transiently expressed in one or both cell lines, and therefore are appropriate for use as complementing agents.

The screening procedure included a positive control, a myc-tagged chloramphenicol acetyltransferase (CAT) gene that allowed the estimation of the detection limit of protein. Based on a CAT-specific ELISA (Boehringer Mannheim, Inc.) about 1.5 ng of myc-tagged CAT fusion protein could be detected as weak but specific band in the Western blot with the myc monoclonal antibody. Accordingly, the above-described screening approach is extremely sensitive, and is suitable for screening all candidate poxvirus genes for suitability as complementing agents.

It is to be understood that the description, specific examples and figures, while indicating preferred embodiments, are given by way of illustration and exemplification and are not intended to limit the present invention. Various changes and modifications within the present invention will become apparent to the skilled artisan from the discussion and disclosure contained herein.

What is claimed is:

1. A defective poxvirus that lacks a function imparted by an essential region of its parental poxvirus, said defective poxvirus comprising a foreign DNA polynucleotide under transcriptional control of a promoter.

2. A defective poxvirus according to claim 1, wherein said promoter is operable with enzymes of said defective poxvirus.

3. A defective poxvirus according to claim 1, wherein said promoter is a poxvirus promoter.

4. A defective poxvirus according to claim 1, wherein said foreign DNA polynucleotide is inserted into said essential region.

5. A defective poxvirus according to claim 1, wherein said essential region has been deleted from said defective poxvirus.

6. A defective poxvirus according to claim 5, wherein a marker replaces said essential region.

7. A defective poxvirus according to claim 6, wherein said foreign DNA polynucleotide is inserted into said marker.

8. A defective poxvirus according to claim 1, wherein said parental poxvirus is an orthopoxvirus.

9. A defective poxvirus according to claim 1, wherein said parental poxvirus is vaccinia.

10. A defective poxvirus according to claim 9, wherein said essential region is an open reading frame selected from the group consisting of I7L, F18R, D13L, D6R, A8L, J1R, E7L, F11L, E4L, I1L, J3R, J4R, H7R, D4R and A6R.

11. A cell line having the ability to complement a lost essential function of a defective poxvirus.

12. A cell line according to claim 11, wherein said ability is imparted by an essential region of a parental poxvirus of said defective poxvirus.

13. A method of producing a protein, comprising the steps of:
    providing a defective poxvirus that lacks a function imparted by an essential region of its parental poxvirus, wherein said defective poxvirus comprises a foreign DNA polynucleotide encoding said protein and said DNA polynucleotide is under transcriptional control of a promoter;
    infecting a complementing cell line with said defective poxvirus; and
    harvesting said protein.

14. A method according to claim 13, wherein said promoter is operable with enzymes of said defective poxvirus.

15. A method according to claim 13, wherein said promoter is a poxvirus promoter.

16. A method according to claim 13, wherein said providing step is accomplished by inserting said DNA polynucleotide into said essential region of said parental poxvirus.

17. A method according to claim 13, wherein said providing step is accomplished by replacing said essential region of said parental poxvirus with said DNA polynucleotide.

18. A method according to claim 13, wherein said providing step is accomplished by replacing said essential region of said parental poxvirus with a marker.

19. A method according to claim 18, wherein said DNA polynucleotide is inserted into said marker.

20. A method according to claim 18, wherein said DNA polynucleotide replaces said marker.

21. A method according to claim 18, wherein said marker is a gpt gene.

22. A method according to claim 13, wherein said parental poxvirus is an orthopoxvirus.

23. A method according to claim 22, wherein said parental poxvirus is vaccinia.

24. A defective poxvirus according to claim 10, wherein the essential region is open reading frame D4R.

25. A defective poxvirus according to claim 1, wherein the foreign DNA polynucleotide is of animal origin.

26. A defective poxvirus according to claim 1, wherein the foreign DNA polynucleotide is of plant origin.

27. A defective poxvirus according to claim 1, wherein the foreign DNA polynucleotide is of bacterial origin.

28. A defective poxvirus according to claim 1, wherein the foreign DNA polynucleotide is of viral origin.

29. A defective poxvirus according to claim 1, wherein the foreign DNA polynucleotide is of fungal origin.

30. A defective poxvirus according to claim 1, wherein the foreign DNA polynucleotide is of protozoan origin.

31. A defective poxvirus according to claim 1, wherein the foreign DNA polynucleotide is synthetic.

32. A defective poxvirus according to claim 1, wherein the foreign DNA polynucleotide is a chimeric gene.

33. A cell line according to claim 12, wherein the cell line is based on RK 13 cells.

34. A cell line according to claim 12, wherein the cell line is based on CV-1 cells.

35. A cell line according to claim 12, wherein the cell line is based on Vero cells.

36. A cell line according to claim 12, wherein the cell line is based on 293 cells.

37. A cell line according to claim 12, wherein the cell line is based on MRC-5 cells.

38. A cell line according to claim 12, wherein the cell line is based on BSC-1 cells.

39. A cell line according to claim 12, wherein the cell line is based on LM (TK$^-$) cells.

40. A cell line according to claim 12, wherein the cell line is based on STO cells.

41. A method according to claim 13, wherein the protein is from a pathogen.

42. A method according to claim 41, wherein the protein is from a bacterial, viral, fungal or protozoan source.

43. A method according to claim 13, wherein the cell line is based on RK 13 cells, CV-1 cells or Vero cells.

44. A method according to claim 13, wherein the cell line is based on 293, MRC-5 cells, BSC-1 cells, LM (TK$^-$) cells or STO cells.

* * * * *